(12) United States Patent
Cincotta et al.

(10) Patent No.: US 10,688,094 B2
(45) Date of Patent: *Jun. 23, 2020

(54) BROMOCRIPTINE FORMULATIONS

(71) Applicant: VeroScience LLC, Tiverton, RI (US)

(72) Inventors: Anthony H. Cincotta, Tiverton, RI (US); Craig Michael Bowe, Encinitas, CA (US); Paul Clark Stearns, San Diego, CA (US); Laura Jean Weston, Escondido, CA (US)

(73) Assignee: VeroScience LLC, Tiverton, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,463

(22) Filed: Apr. 24, 2019

(65) Prior Publication Data

US 2019/0343833 A1 Nov. 14, 2019

Related U.S. Application Data

(63) Continuation of application No. 15/981,752, filed on May 16, 2018, now Pat. No. 10,307,421, which is a continuation of application No. 15/618,055, filed on Jun. 8, 2017, now Pat. No. 9,993,474, which is a continuation of application No. 15/286,826, filed on Oct. 6, 2016, now Pat. No. 9,700,555, which is a
(Continued)

(51) Int. Cl.
| | |
|---|---|
| *A61K 31/4985* | (2006.01) |
| *A61K 31/48* | (2006.01) |
| *A61K 9/20* | (2006.01) |
| *A61K 9/14* | (2006.01) |

(52) U.S. Cl.
CPC ............ *A61K 31/4985* (2013.01); *A61K 9/14* (2013.01); *A61K 9/2009* (2013.01); *A61K 9/2013* (2013.01); *A61K 9/2018* (2013.01); *A61K 9/2059* (2013.01); *A61K 9/2072* (2013.01); *A61K 9/2077* (2013.01); *A61K 9/2095* (2013.01); *A61K 31/48* (2013.01)

(58) Field of Classification Search
CPC .................................................. A61K 31/4985
See application file for complete search history.

(56) References Cited

U.S. PATENT DOCUMENTS

| | | | |
|---|---|---|---|
| 4,659,715 | A | 4/1987 | Meier et al. |
| 4,783,469 | A | 11/1988 | Meier et al. |
| | | (Continued) | |

FOREIGN PATENT DOCUMENTS

| | | |
|---|---|---|
| CN | 1678313 | 10/2005 |
| JP | 9-510955 | 11/1997 |
| | (Continued) | |

OTHER PUBLICATIONS

Armentero et al., "Dopamine Receptor Agonists Media europrotection in malonate-Induced striatal lesion in the Rat," Experimental Neurology, Dec. 2002, 178(2):301-305.
(Continued)

*Primary Examiner* — Benjamin J Packard
(74) *Attorney, Agent, or Firm* — Fish & Richardson P.C.

(57) ABSTRACT

The present application describes pharmaceutical formulations of bromocriptine mesylate and methods of manufacturing and using such formulations. The formulations are useful for improving glycemic control in the treatment of type 2 diabetes.

30 Claims, 5 Drawing Sheets

Related U.S. Application Data continuation of application No. 14/920,123, filed on Oct. 22, 2015, now Pat. No. 9,522,117, which is a continuation of application No. 14/088,269, filed on Nov. 22, 2013, now Pat. No. 9,192,576, which is a continuation of application No. 13/773,500, filed on Feb. 21, 2013, now Pat. No. 8,613,947, which is a continuation of application No. 13/460,452, filed on Apr. 30, 2012, now Pat. No. 8,431,155.

(56) References Cited

U.S. PATENT DOCUMENTS

| | | | |
|---|---|---|---|
| 4,791,125 | A | 12/1988 | Clark |
| 5,006,526 | A | 4/1991 | Meier et al. |
| 5,066,495 | A | 11/1991 | Moro et al. |
| 5,344,832 | A | 9/1994 | Cincotta et al. |
| 5,468,755 | A | 11/1995 | Cincotta et al. |
| 5,554,623 | A | 9/1996 | Cincotta et al. |
| 5,565,454 | A | 10/1996 | Cincotta |
| 5,585,347 | A | 12/1996 | Meier et al. |
| 5,626,860 | A | 5/1997 | Cincotta et al. |
| 5,635,512 | A | 6/1997 | Cincotta et al. |
| 5,654,313 | A | 8/1997 | Cincotta et al. |
| 5,668,155 | A | 9/1997 | Cincotta et al. |
| 5,679,685 | A | 10/1997 | Cincotta et al. |
| 5,688,794 | A | 11/1997 | Meier et al. |
| 5,696,128 | A | 12/1997 | Cincotta et al. |
| 5,700,795 | A | 12/1997 | Cincotta et al. |
| 5,700,800 | A | 12/1997 | Cincotta et al. |
| 5,712,265 | A | 1/1998 | Cincotta et al. |
| 5,714,519 | A | 2/1998 | Cincotta et al. |
| 5,716,957 | A | 2/1998 | Cincotta et al. |
| 5,716,962 | A | 2/1998 | Cincotta et al. |
| 5,719,160 | A | 2/1998 | Cincotta et al. |
| 5,731,312 | A | 3/1998 | Cincotta et al. |
| 5,741,503 | A | 4/1998 | Cincotta et al. |
| 5,744,477 | A | 4/1998 | Cincotta et al. |
| 5,750,519 | A | 5/1998 | Cincotta et al. |
| 5,756,513 | A | 5/1998 | Cincotta et al. |
| 5,760,047 | A | 6/1998 | Cincotta et al. |
| 5,792,748 | A | 8/1998 | Cincotta et al. |
| 5,830,895 | A | 11/1998 | Cincotta et al. |
| 5,854,255 | A | 12/1998 | Cincotta et al. |
| 5,866,584 | A | 2/1999 | Cincotta et al. |
| 5,872,127 | A | 2/1999 | Cincotta et al. |
| 5,872,133 | A | 2/1999 | Cincotta et al. |
| 5,877,183 | A | 3/1999 | Cincotta |
| 5,902,811 | A | 5/1999 | Cincotta |
| 5,905,083 | A | 5/1999 | Cincotta et al. |
| 6,004,972 | A | 12/1999 | Cincotta et al. |
| 6,071,914 | A | 6/2000 | Cincotta et al. |
| 6,075,020 | A | 6/2000 | Cincotta et al. |
| 6,855,707 | B2 | 2/2005 | Cincotta |
| 7,572,789 | B2 | 8/2009 | Cowen et al. |
| 7,888,310 | B2 | 2/2011 | Cincotta |
| 8,021,681 | B2 | 9/2011 | Cincotta |
| 8,137,992 | B2 | 3/2012 | Cincotta |
| 8,137,993 | B2 | 3/2012 | Cincotta |
| 8,137,994 | B2 | 3/2012 | Cincotta |
| 8,431,155 | B1 | 4/2013 | Cincotta et al. |
| 8,613,947 | B2 | 12/2013 | Cincotta et al. |
| 8,741,918 | B2 | 6/2014 | Cincotta |
| 8,821,915 | B2 | 9/2014 | Cincotta |
| 8,877,708 | B2 | 11/2014 | Cincotta |
| 9,192,576 | B2 | 11/2015 | Cincotta et al. |
| 9,205,084 | B2 | 12/2015 | Cincotta |
| 2001/0016582 | A1 | 8/2001 | Cincotta et al. |
| 2002/0187985 | A1 | 12/2002 | Cincotta |
| 2004/0077679 | A1 | 4/2004 | Cincotta |
| 2004/0081678 | A1 | 4/2004 | Cincotta |
| 2004/0214887 | A1 | 10/2004 | Dasseux et al. |
| 2004/0220190 | A1 | 11/2004 | Cincotta |
| 2005/0054652 | A1 | 3/2005 | Cincotta |
| 2005/0054734 | A1 | 3/2005 | Cincotta |
| 2005/0215558 | A1 | 9/2005 | Cincotta |
| 2008/0200453 | A1 | 8/2008 | Cincotta |
| 2008/0293735 | A1 | 11/2008 | Cincotta |
| 2009/0137598 | A1 | 5/2009 | Cincotta |
| 2009/0143390 | A1 | 6/2009 | Cincotta |
| 2010/0035886 | A1 | 2/2010 | Cincotta et al. |
| 2013/0197005 | A1 | 8/2013 | Cincotta |
| 2013/0274246 | A1 | 10/2013 | Cincotta |
| 2014/0051685 | A1 | 2/2014 | Cincotta |
| 2014/0249136 | A1 | 9/2014 | Cincotta |
| 2014/0342975 | A1 | 11/2014 | Cincotta |
| 2015/0011554 | A1 | 1/2015 | Cincotta et al. |
| 2015/0024995 | A1 | 1/2015 | Cincotta |
| 2015/0335641 | A1 | 11/2015 | Cincotta |
| 2016/0038424 | A1 | 2/2016 | Cincotta et al. |

FOREIGN PATENT DOCUMENTS

| | | | |
|---|---|---|---|
| JP | 9-511255 | 11/1997 | |
| JP | 2006-527261 | 11/2006 | |
| JP | 2008-531678 | 8/2008 | |
| JP | 2010-523688 | 7/2010 | |
| KR | 20100091944 | 8/2010 | |
| RU | 2467743 | 11/2012 | |
| WO | WO 1995/017170 | 6/1995 | |
| WO | WO 1996/013251 | 5/1996 | |
| WO | WO 2004/010946 | 2/2004 | |
| WO | WO 2004/110407 | 12/2004 | |
| WO | WO 2006/092727 | 9/2006 | |
| WO | WO 2007/119792 | 10/2007 | |
| WO | WO 2008/127794 | 10/2008 | |
| WO | WO 2009/091576 | 7/2009 | |
| WO | WO-2009091576 A2 * | 7/2009 | ........... A61K 9/0019 |
| WO | WO 2010/141938 | 12/2010 | |

OTHER PUBLICATIONS

Arteriosclerosis/atherosclerosis Definition—Diseases and Condition, By Mayo Clinic staff, May 2014, accessed on Oct. 8, 2014; available at http://www.mayoclinic.org/diseases-conditions/arteriosclerosis-atherosclerosis/basics/definition/con-20026972, 9 pages.

Breen et al., "Insulin increases reendothelialization and inhibits cell migration and neointimal growth after arterial injury," Arterioscler Thromb Vasc Biol. 2009, 29:1060-1066.

Bruemmer et al., "Thiazolidinedione regulation of smooth muscle cell proliferation," The American Journal of Medicine, Dec. 8, 2003, 115(BA):87S-92S.

Dai et al., "LOX-1, a bridge between GLP-1 and mitochondrial ROS generation in human vascular smooth muscle cells," Biochemical and Biophysical Research Communications, 2013, 437:62-66.

Dios et al., "Troglitazone, but not rosiglitazone, inhibits na/h exchange activity and proliferation of macrovascular endothelial cells," Journal of Diabetes and its Complications, 2001, 15:120-127.

Dormandy et al., "Secondary prevention of macrovascular events in patients with type 2 diabetes in the PROactive Study (PROspective pioglitazone Clinical Trial In macrovascular events): a randomised controlled trial," Lancet, Oct. 8. 2005, 366:1279-89.

Dubey et al., "Pioglitazone attenuates hypertension and inhibits growth of renal arteriolar smooth muscle in rats," American Physiological Society, 1993, R726-R732.

Duckworth et al., "Glucose control and vascular complications in veterans with type 2 diabetes," The New England Journal of Medicine, Jan. 8, 2009, 360:129-139.

Ervinna et al., "Anagliptin, a dpp-4 inhibitor, suppresses proliferation of vascular smooth muscles and monocyte inflammatory reaction and attenuates atherosclerosis in male apo e-deficient mice," Endocrinology, Mar. 2013, 145(3):1260-1270.

Fukuda et al., "Troglitazone inhibits growth and improves insulin signaling by suppression of angiotensin ii action in vascular smooth muscle cells from spontaneously hypertensive rats," Atherosclerosis, 2002, 163:229-239.

Gaziano et al., "Effect of bromocriptine-qr (a quick-release formulation of bromocriptine mesylate) on major adverse cardiovascular events in type 2 diabetes subjects," J Am Heart Assoc, 2012, 1:doi:10.1161/JAHA.112.002279, 11 pages.

(56) References Cited

OTHER PUBLICATIONS

Gaziano et al., "Randomized clinical trial of quick-release bromocriptine among patients with type 2 diabetes on overall safety and cardiovascular outcomes," Diabetes Care, Jul. 2010, 33:1503-1508 (12 total pages).
Gerstein et al., "Effects of intensive glucose lowering in type 2 diabetes," The New England Journal of Medicine, Jun. 12, 2008, 358:2545-59.
Gerstein, "Basal insulin and cardiovascular and other outcomes in dysglycemia," The New England Journal of Medicine, Jul. 26, 2012, 367:319-328.
Goto et al., "Exendin-4, a glucagon-like peptide-1 receptor agonist, reduces intimal thickening after vascular injury," Biochemical and Biophysical Research Communications, 2011, 405:79-84.
Gouni-Berthold et al., "Troglitazone and rosiglitazone inhibit the low density lipoprotein-induced vascular smooth muscle cell growth," Exp Clin Endocrinol Diabetes, 2001, 109:203-209.
Ha et al., "High glucose induces connective tissue growth factor expression and extracellular matrix accumulation in rat aorta vascular smooth muscle cells via extracellular signal-regulated kinase 1 / 2," Korean J Physiol Pharmacol, Aug. 2013, 17:307-314.
Hara et al., "Central dopaminergic function in stroke prone spontaneously hypertensive rats effects of chronic treatment with lisuride on the impaired swimming ability," Database Accession No. PREV198376013141 and Folia Pharmacologica Japonica, 1982, 80(5):395-394 (Abstract only—2 pages).
Hasko et al., "Modulation of lipopolysaccharide-induced tumor necrosis factor-α and nitric oxide production by dopamine receptor agonists and antagonists in mice," Immunology Letters, 1996, 49(3):143-147.
Home et al., "Rosiglitazone evaluated for cardiovascular outcomes in oral agent combination therapy for type 2 diabetes (record): a multicentre, randomised, open-label trial," Lancet, Jun. 20, 2009, 373:2125-35.
Hsueh et al., "Insulin signaling in the arterial wall," Am J Cardiol, 1999, 84:21J-24J.
Kalra et al., "Dopamine: the forgotten felon in type 2 diabetes," Recent Pat Endocr Metab Immune Drug Discov., 5(1):61-65, Jan. 2011.
Kuo et al., "Hypothalamic neuropeptide Y (NPY) and the attenuation of hyperphagia in streptozotocin diabetic rats treated with dopamine D1/D2 agonists," British Journal of Pharmacology, 2006, 148:640-647.
Lan et al., "Vascular fibrosis in atherosclerosis," Cardiovascular Pathology, 2013, 22:4101-407.
Lightell et al., "Loss of canonical insulin signaling accelerates vascular smooth muscle cell proliferation and migration through changes in p27kip1 regulation," Endocrinology, Feb. 2011, 152(2):651-658.
Lusis, "Atherosclerosis," Nature, 407(6801): 233-241, Sep. 14, 2000 [author manuscript].
NCBI Reference Sequence XP-002587257, Hypothetical Protein BRAFLDRAFT-61678 (*Branchiostoma floridae*), Accession No. XP_002587257, GI No. 260784404, dated Oct. 8, 2009, (retrieved from the Internet: Feb. 23, 2015), 2 pages.
O'Neill et al., "Dopamine D2 receptor agonists protect against ischaemia induced hippocampal neurodegeneration in global cerebral ischaemia," European Journal of Pharmacology, Jul. 3, 1998, 352(1):37-46.
Park et al., "The inhibition of insulin-stimulated proliferation of vascular smooth muscle cells by rosiglitazone is mediated by the akt-mtor-p70s6k pathway," Yonsei Med J, 2008, 49(4):592-600.
Patel et al., "Intensive blood glucose control and vascular outcomes in patients with type 2 diabetes," The New England Journal of Medicine, Jun. 6, 2008, 358:2560-72.
Pijl and Meinders, "Modulation of monoaminergic neural circuits: potential for the treatment of type 2 diabetes mellitus," Treat Endocrine, 2002, 1(2):71-78.

Ratner et al., "Cardiovascular safety of exenatide BID: an integrated analysis from controlled clinical trials in participants with type 2 diabetes," Cardiovascular Diabetology, 2011, 10:22, 10 pages.
Santarus, Inc., Cycloset Prescribing Information, 13 pp., (2010).
Santarus, Inc., Santarus Announces Commercial Launch of of Novel Type 2 Diabetes Drug CYCLOSET. 2 pp., (2010).
Schaper et al., "Peripheral vascular disease and Type 2 diabetes mellitus," Diabetes Metab Res Rev, 2000, 16(Suppl 1) S11-S15.
Schobel et al., "Effects of bromocriptine on cardiovascular regulation in healthy humans," *Hypertension*, 25(5):1075-1082, May 1995.
Scirica et al., "Saxagliptin and cardiovascular outcomes in patients with type 2 diabetes mellitus," The New England Journal of Medicine, Oct. 3, 2013, 369(14):1317-1326.
Stout, "Insulin as a mitogenic factor: role in the pathogenesis of cardiovascular disease," The American Journal of Medicine, Feb. 21, 1991, 90 (suppl 2A—62S-65S).
Takasawa, "Inhibition of dipeptidyl peptidase 4 regulates microvascular endothelial growth induced by inflammatory cytokines," Biochemical and Biophysical Research Communications, 2010, 401:7-12.
Turner, "Intensive blood-glucose control with sulphonylureas or insulin compared with conventional treatment and risk of complications in patients with type 2 diabetes (UKPDS 33)," UK Prospective Diabetes Study D (UKPDS) Group, The Lancet, Sep. 12, 1998, 352:837-853.
Veroscience, LLC, Prior Approval Supplement for CMC Change Utilization of Micronized Bromocriptine Mesylate (Redacted), 22 pp. (2012).
White et al., "Alogliptin after acute coronary syndrome in patients with type 2 diabetes," The New England Journal of Medicine, Oct. 3, 2013, 369(14):1327-1335.
Zou et al., "Protein-protein coupling/uncoupling enables dopamine d2 receptor regulation of AMPA receptor-mediated excitotoxicity," The Journal of Neuroscience, Apr. 27, 2005, 25(17):4385-4395.
AU Office Action in Australian Appln. No. 2018203021, dated Feb. 13, 2019, 3 pages.
BR Office Action in Brazilian Appln. BR1120140270872, dated Jul. 30, 2019, 4 pages.
Decision to Grant a Patent in Application No. 2015-510364, dated Jul. 27, 2017, 6 pages.
Decision to Grant in European Appln. No. 13721874.9, dated Aug. 16, 2019, 2 pages.
International Preliminary Report on Patentability for PCT/US2013/038655, dated Nov. 4, 2014, 7 pages.
International Search Report and Written Opinion dated Jul. 2, 2013, which issued in corresponding International Application No. PCT/US2013/038655, 12 pages.
Non Final Office Action in U.S. Appl. No. 14/920,123, dated Jan. 22, 2016, 11 pages.
Non-final Office Action in U.S. Appl. No. 13/460,452, dated Sep. 17, 2012, 11 pages.
Non-final Office Action in U.S. Appl. No. 13/773,500, dated May 2, 2013, 12 pages.
Non-final Office Action in U.S. Appl. No. 14/088,269, dated Dec. 5, 2014, 10 pages.
Notice of Acceptance in Australian Application No. 2013256558, dated Jan. 14, 2016, 3 pages.
Notice of Allowance for Korean Application No. 10-2014-7033501.
Notice of Allowance in Canadian Application No. 2872300, dated Dec. 16, 2015, 1 page.
Notice of Allowance in U.S. Appl. No. 13/460,452, dated Mar. 6, 2013, 13 pages.
Notice of Allowance in U.S. Appl. No. 13/773,500, dated Nov. 19, 2013, 3 pages.
Notice of Allowance in U.S. Appl. No. 13/773,500, dated Sep. 16, 2013, 10 pages.
Notice of Allowance in U.S. Appl. No. 14/088,269, dated Jul. 27, 2015, 13 pages.
Office Action in Australian Application No. 2013256558, dated Jan. 30, 2015, 2 pages.
Office Action in Australian Application No. 2016202572, dated Jan. 27, 2017.

(56) References Cited

OTHER PUBLICATIONS

Office Action in Canadian Application No. 2872300, dated May 27, 2015, 3 pages.
Office Action in European Application No. 13721874.9, dated Dec. 9, 2014, 2 pages.
Office Action in European Application No. 13721874.9, dated Jan. 5, 2017.
Office Action in GCC Application No. GC 2013-24255, dated Jul. 6, 2017.
Office Action in Gulf Coop Council No. 2013-24255, dated Aug. 30, 2016.
Office Action in Japanese Application No. 2015-510364, dated Jan. 24, 2017, 13 pages (with English translation).
Office Action in Japanese Application No. 2015-510364, dated Jun. 14, 2016, 15 pages.
Office Action in Korean Application No. 10-2014-7033501, dated Mar. 11, 2015, 23 pages.
Office Action in Mexican Application No. MX/a/2014/013158, dated Apr. 4, 2018 (with English translation).

\* cited by examiner

BROMOCRIPTINE FORMULATIONS

CROSS-REFERENCE TO RELATED APPLICATIONS

This application is a continuation of U.S. application Ser. No. 15/981,752, filed May 16, 2018, which is a continuation of U.S. application Ser. No. 15/618,055, filed Jun. 8, 2017, now U.S. Pat. No. 9,993,474, which is a continuation of U.S. application Ser. No. 15/286,826, filed Oct. 6, 2016, now U.S. Pat. No. 9,700,555, which is a continuation of U.S. application Ser. No. 14/920,123, filed Oct. 22, 2015, now U.S. Pat. No. 9,522,117, which is a continuation of U.S. application Ser. No. 14/088,269, filed Nov. 22, 2013, now U.S. Pat. No. 9,192,576, which is a continuation of U.S. application Ser. No. 13/773,500, filed Feb. 21, 2013, now U.S. Pat. No. 8,613,947, which is a continuation of U.S. application Ser. No. 13/460,452, filed Apr. 30, 2012, now U.S. Pat. No. 8,431,155, the entire content of each of which is incorporated herein by reference.

TECHNICAL FIELD

This invention relates to pharmaceutical formulations and methods of their manufacture and use, and more particularly to formulations of bromocriptine mesylate that are useful for treating type 2 diabetes.

BACKGROUND

Bromocriptine ((5'α)-2-bromo-12'-hydroxy-2'-(1-methylethyl)-5'-(2-methylpropyl)-ergotaman-3',6',18-trione, CAS Registry No. 25614-03-3) is an ergot alkaloid which is a potent dopamine D2 receptor agonist. The compound has the following formula:

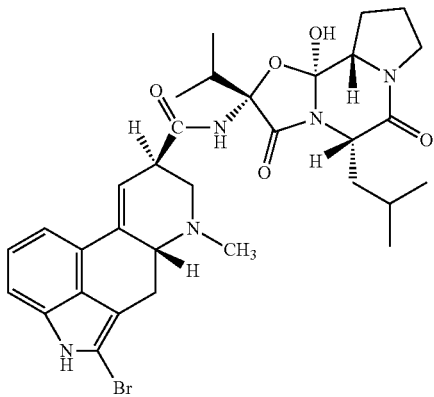

Solid oral dosage forms of bromocriptine are available as bromocriptine mesylate ((5'α)-2-bromo-12'-hydroxy-2'-(1-methylethyl)-5'-(2-methylpropyl)-ergotaman-3',6',18-trione monomethanesulfonate salt, CAS Registry No. 22260-51-1) in a tablet containing up to 2.5 mg bromocriptine or in capsule form containing 5 mg bromocriptine. Bromocriptine is useful in the treatment of certain hyperprolactinemia-associated dysfunctions and acromegaly, in the prevention of physiological lactation, and in the treatment of Parkinson's disease and prevention of tolerance to Levodopa therapy for Parkinson's disease. In clinical trials, adverse effects included nausea, headache, dizziness, fatigue, lightheadedness, vomiting, abdominal cramps, nasal congestion, constipation, diarrhea and drowsiness. When bromocriptine is used as described above, prolactin is reduced to low levels throughout a 24 hour period.

U.S. Pat. Nos. 5,344,832, 5,554,623 and 5,716,957 discuss a method for modifying and regulating lipid and glucose metabolism by administering a dopamine agonist, e.g., bromocriptine, and/or a prolactin stimulator to reset hormonal timing in the neural centers of the brain to control insulin resistance, hyperinsulinemia and hyperglycemia.

U.S. Pat. Nos. 5,468,755, 5,756,513 and 5,866,584 discuss a method to modify and regulate lipid and carbohydrate metabolism-generally to reduce obesity, insulin resistance, hyperinsulinemia and hyperglycemia, by administration of a dopamine agonist such as bromocriptine to inhibit prolactin over a limited period at a time of day to reset normal hormonal timing and control insulin resistance, hyperinsulinemia and hyperglycemia.

U.S. Pat. No. 5,679,685 discusses accelerated release bromocriptine mesylate formulations for regulating prolactin levels that are abnormal during particular times during the day.

WO/2009/091576 discusses compositions for parenteral administration using dopamine agonists such as bromocriptine, that are described as being useful for treating metabolic-related conditions such as type 2 diabetes.

CYCLOSET®, a tablet form of bromocriptine mesylate providing a 0.8 mg dose of bromocriptine, is FDA approved for once-daily administration to improve glycemic control in adults with type 2 diabetes mellitus, at a dose of 2-6 tablets (1.6 to 4.8 mg total dose).

SUMMARY

In one aspect, the present application provides an oral dosage form, for example a tablet, which includes micronized bromocriptine mesylate and one or more excipients. The micronized bromocriptine mesylate is present in an amount that provides a dose of at least about 0.8 mg of bromocriptine per dosage form and has Dv90 of less than about 10 µm. The dosage form provides a dissolution profile, when tested in USP Apparatus Type 2 Paddle Method at 50 rpm in 500 mL of 0.1 N hydrochloric acid at about 37° C., wherein at least about 90% of the bromocriptine mesylate has been released at about 30 minutes.

In a further aspect, the present application provides a further method for the manufacture of a bromocriptine mesylate tablet. The method includes processing bromocriptine mesylate to reduce the average particle size of the bromocriptine mesylate to provide bromocriptine mesylate that has a Dv90 of less than about 20 µm and blending the processed bromocriptine mesylate with excipients to form a mixture wherein the bromocriptine mesylate is substantially evenly distributed in the mixture. The mixture is compressed to form a tablet. The tablet includes bromocriptine mesylate in an amount that provides a dose of at least about 0.8 mg of bromocriptine; and provides a dissolution profile, when tested in USP Apparatus Type 2 Paddle Method at 50 rpm in 500 mL of 0.1 N hydrochloric acid at about 37° C., wherein at least about 90% of the bromocriptine mesylate has been released at about 30 minutes.

In another aspect, the present application provides a method for the manufacture of a bromocriptine mesylate tablet. The method includes determining that bromocriptine mesylate has a particle size distribution equivalent to a volume-based particle size distribution with a Dv90 of less than about 20 µm, blending the bromocriptine mesylate of determined particle size distribution with excipients to form a mixture wherein the bromocriptine mesylate is substantially evenly distributed in the mixture. The mixture is compressed to form a tablet. The tablet includes bromocriptine mesylate in an amount that provides a dose of at least about 0.8 mg of bromocriptine; and provides a dissolution profile, when tested in USP Apparatus Type 2 Paddle Method at 50 rpm in 500 mL of 0.1 N hydrochloric acid at about 37° C., wherein at least about 90% of the bromocriptine mesylate has been released at about 30 minutes.

In another aspect, the present application provides a method of treatment for improving glycemic control in a type 2 diabetes patient. The method includes administering a bromocriptine mesylate oral dosage form, for example a tablet, which includes micronized bromocriptine mesylate and one or more excipients. The micronized bromocriptine mesylate is present in an amount that provides a dose of at least about 0.8 mg of bromocriptine per dosage form and has Dv90 of less than about 10 µm. The dosage form provides a dissolution profile, when tested in USP Apparatus Type 2 Paddle Method at 50 rpm in 500 mL of 0.1 N hydrochloric acid at about 37° C., wherein at least about 90% of the bromocriptine mesylate has been released at about 30 minutes.

In another aspect, the present application provides a further method of treatment for improving glycemic control in a type 2 diabetes patient. The method includes processing bromocriptine mesylate to reduce the average particle size of the bromocriptine mesylate to provide bromocriptine mesylate that has a Dv90 of less than about 20 µm and blending the processed bromocriptine mesylate with excipients to form a mixture wherein the bromocriptine mesylate is substantially evenly distributed in the mixture. The mixture is compressed to form a tablet. The tablet includes bromocriptine mesylate in an amount that provides a dose of at least about 0.8 mg of bromocriptine; and provides a dissolution profile, when tested in USP Apparatus Type 2 Paddle Method at 50 rpm in 500 mL of 0.1 N hydrochloric acid at about 37° C., wherein at least about 90% of the bromocriptine mesylate has been released at about 30 minutes. The tablet is provided for administration to the patient.

In another aspect, the present application provides a further method of treatment for improving glycemic control in a type 2 diabetes patient. The method includes determining that bromocriptine mesylate has a particle size distribution equivalent to a volume-based particle size distribution with a Dv90 of less than about 20 µm, blending the bromocriptine mesylate of determined particle size distribution with excipients to form a mixture wherein the bromocriptine mesylate is substantially evenly distributed in the mixture. The mixture is compressed to form a tablet. The tablet includes bromocriptine mesylate in an amount that provides a dose of at least about 0.8 mg of bromocriptine; and provides a dissolution profile, when tested in USP Apparatus Type 2 Paddle Method at 50 rpm in 500 mL of 0.1 N hydrochloric acid at about 37° C., wherein at least about 90% of the bromocriptine mesylate has been released at about 30 minutes. The tablet is provided for administration to the patient.

The details of one or more embodiments of the invention are set forth in the accompanying drawings and the description below. Other features, objects, and advantages will be apparent from the description and drawings, and from the claims.

DETAILED DESCRIPTION

Figure 1:
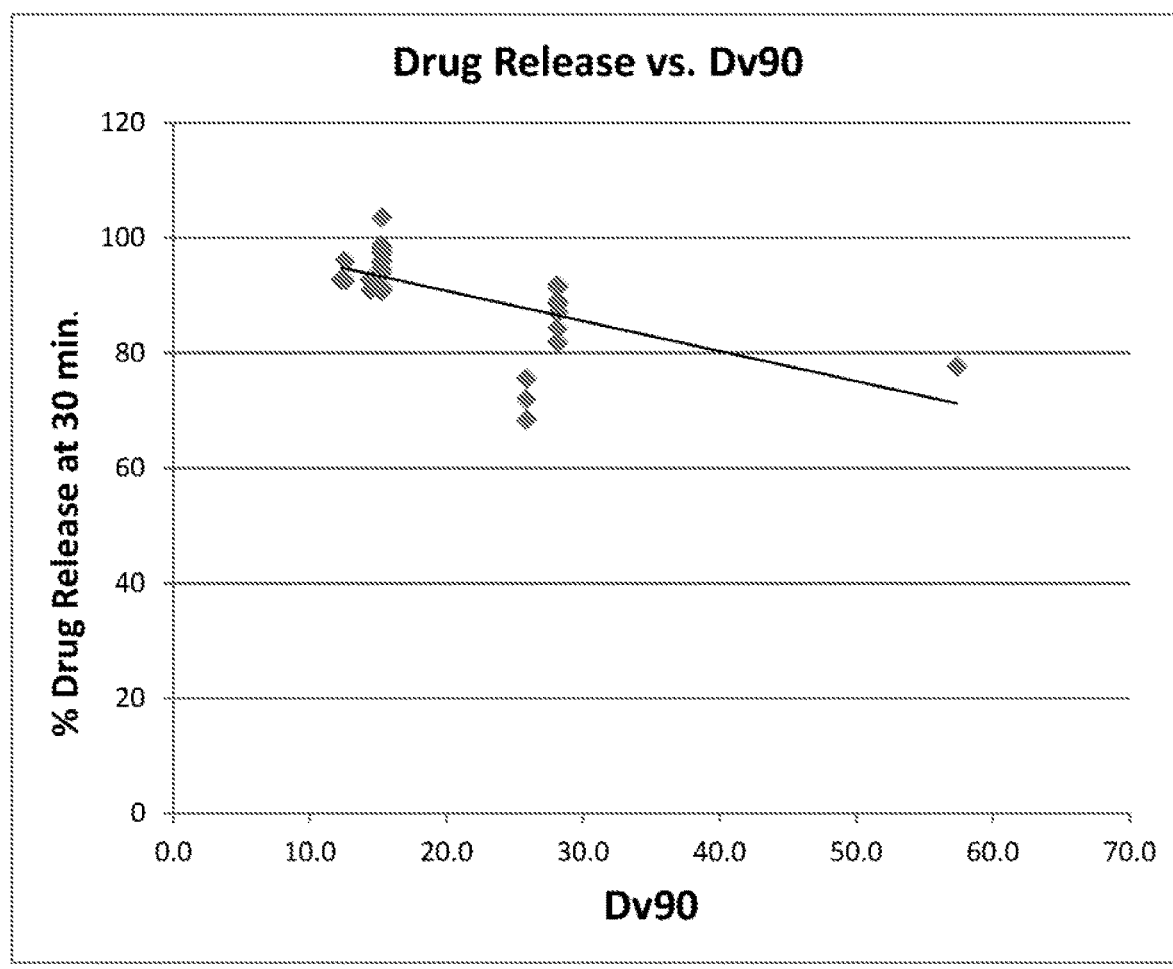
FIG. 1 is a plot showing the correlation between release of bromocriptine mesylate at about 30 minutes for various batches of bromocriptine mesylate tablets and the Dv90 of the bromocriptine mesylate particles from which the batches were prepared.

"About," as used herein, means approximately, e.g., plus or minus approximately ten percent of the indicated value.

"Particle," as used herein, refers to an aggregated physical unit of a compound (e.g., bromocriptine mesylate), i.e., a piece or a grain.

"Particle size" as used herein, refers to the average linear dimension of a particle of a compound, for example the diameter of a spherical particle of a compound.

"Micronization," as used herein, refers to a process of reducing the average particle size of a solid material, typically to provide particles with a particle size of a few micrometers.

"Micronized," as used herein, refers to a material that has been subjected to micronization.

The term "oral dosage form" refers to a drug dosage form that provides for absorption of a substantial amount of the drug through the gastric and/or intestinal mucosa of the gastrointestinal tract.

The term "tablet" refers to an oral dosage form that comprises a mixture of active substances and excipients, usually in powder form, pressed or compacted from a powder into a solid dose.

"Particle size distribution" as used herein refers to the relative proportions of particles of a compound, such as bromocriptine mesylate, having a given particle size. While the particle size of a spherical object can be unambiguously and quantitatively defined by its diameter, particles comprising an active pharmaceutical ingredient, such as bromocriptine mesylate for example, may be non-spherical and irregular in shape. There are several methods by which those of ordinary skill in the art measure and express the size of non-spherical and irregular particles, such as measuring the size of such particles using laser diffractometry and expressing the size of such particles based on replacing a given particle with an imaginary sphere that has one of a number of properties of the particle. Such properties can be selected from, for example, but are not limited to, the diameter of an imaginary sphere having the same volume of the particle being measured (volume-based particle size), the diameter of an imaginary sphere having the same weight as the particle being measured (weight-based particle size), and the diameter of an imaginary sphere having the same surface area as the particle being measured (area-based particle size). Those having ordinary skill in the art are familiar with such methods, and the manner in which the results of such methods are expressed, and such methods can be applied to the embodiments disclosed herein without undue experimentation. The particle size distribution may be represented, for example, graphically as a plot. A common type of plot is a cumulative undersize plot which represents the fraction (e.g. by number, volume or mass) of particles that are smaller than the stated particle size.

The parameters Dv10, Dv50, Dv90 and Dv99 represent the particle size at the 10%, 50%, 90% and 99% points of the cumulative volume undersize particle size distribution. Thus, a "Dv10" for a material represents a particle size wherein 10% of the volume of the material consists of particles having a particle size equal to the Dv10 value or smaller. A "Dv50" for a material represents a particle size wherein 50% of the volume of the material consists of particles having a particle size equal to the Dv50 value or smaller. A "Dv90" for a material represents a particle size wherein 90% of the volume of the material consists of particles having a particle size equal to the Dv90 value or smaller. A "Dv99" for a material represents a particle size wherein 99% of the volume of the material consists of particles having a particle size equal to the Dv99 value or smaller.

The term "span" as used herein means a measure of the width of the distribution of given particle sizes of a given compound comprising an embodiment disclosed herein. In particular, the span of a given embodiment can be provided by measuring the size of the particles of a given compound using a volume-based particle size distribution method and applying the formula below, wherein Dv90, Dv10 and Dv50 are as hereinbefore defined:

$$\text{Span} = \frac{Dv90 - Dv10}{Dv50}$$

The term "treating" or "treatment" as used herein means the treating or treatment of a disease or medical condition (such as type 2 diabetes) in a patient, such as a mammal (particularly a human) that comprises ameliorating the disease or medical condition, i.e., eliminating or causing regression of the disease or medical condition in a patient, suppressing the disease or medical condition, i.e., slowing or arresting the development of the disease or medical condition in a patient; or alleviating the symptoms of the disease or medical condition in a patient.

The present application describes improved bromocriptine mesylate formulations for improving glycemic control and treating type 2 diabetes, manufacturing methods for preparing such formulations, as well as methods of using such formulations. The formulations may contain bromocriptine mesylate in an amount that provides a dose of at least about 0.8 mg, for example about 0.8 mg, of bromocriptine. The bromocriptine mesylate may be present in the formulations as the sole pharmaceutically active ingredient. The bromocriptine mesylate formulations may be oral dosage form, e.g., tablets. The bromocriptine mesylate may substantially evenly distributed in the tablets.

In one aspect, the present application describes that in the preparation of bromocriptine mesylate formulations for improving glycemic control and treating type 2 diabetes, it has been discovered that controlling the size of the bromocriptine mesylate particles in the formulations may affect the potency and safety profile of the bromocriptine mesylate. The present application therefore provides methods for manufacturing bromocriptine tablets comprising bromocriptine mesylate particles having a controlled particle size, which provides a more consistent release of bromocriptine mesylate from the formulation, which release allows the formulation to be therapeutically effective for treating type 2 diabetes.

In some aspects, the present application provides methods for providing bromocriptine mesylate tablets with uniform content, such that the bromocriptine mesylate is uniformly distributed within an ingredient blend that is compressed to form tablets, and each tablet contains substantially the same amount of bromocriptine mesylate and, as a result, provides substantially the same dose of bromocriptine mesylate to the patient. This property is desirable so that bromocriptine tablets provide consistent efficacy, by ensuring that each tablet provides an efficacious amount of the drug, but also does not provide too high a dose of the drug which may lead to side effects.

The mode of action involved in using bromocriptine to improve glycemic control and treating type 2 diabetes presents challenges in developing and manufacturing formulations that are suitable for this purpose. Many drugs work best when the pharmacological action of the drug (e.g., blocking a receptor or inhibiting an enzyme) is maintained throughout the period of treatment. While not being limited by theory, results from preclinical studies suggest that appropriately timed daily administration of bromocriptine in the morning normalizes aberrant hypothalamic neurotransmitter activities that induce, potentiate, and maintain the insulin-resistant, glucose-intolerant state.

Thus, it is believed that a formulation of bromocriptine mesylate manufactured to improve glycemic control and treat type 2 diabetes should provide a consistent, rapid and substantially complete release of the drug from the formulation to provide the optimum pharmacokinetic profile for treating diabetes. For example, while not being limited by theory, formulation of bromocriptine mesylate for improving glycemic control should be formulated in a tablet that provides a dose of at least about 0.8 mg of bromocriptine and which releases at least about 80%, or preferably at least about 90%, or at least about 95%, of the drug within about 30 minutes. Drug release can be measured, for example, using the methods and apparatus described in the U.S. Pharmacopoeia (USP), General Chapter 711, Dissolution, 34$^{th}$ Edition, 2011. A suitable method for measuring release of bromocriptine mesylate from the tablets described in the present application can use USP Apparatus Type 2 Paddle Method at 50 rpm in 500 mL of 0.1 N hydrochloric acid. The dissolution experiment is typically carried out at about 37° C. Unless a product can be manufactured that consistently provides the specified dose and release profile, the resulting product may be less effective for improving glycemic control and treating type 2 diabetes and also may result in increased incidence of side-effects.

An accelerated release formulation of bromocriptine mesylate was described in U.S. Pat. No. 5,679,685, which discusses that accelerated release from bromocriptine mesylate formulations could be achieved by formulating bromocriptine, an antioxidant, a filler, a disintegrating agent, a water scavenging agent and a lubricant. In the preferred formulation, the bromocriptine formulation included bromocriptine mesylate together with citric acid, corn starch, lactose filler and silicon dioxide and magnesium stearate. Use of anhydrous lactose filler is preferred to minimize moisture content. Citric acid is an antioxidant. Corn starch is a disintegrating agent. Colloidal silicone dioxide acts as a water-scavenger. Magnesium stearate acts as a lubricant. While the '685 patent describes the preparation of rapid release bromocriptine mesylate on a laboratory scale, difficulties have been encountered, however, in manufacturing such a formulation on a large scale suitable for commercial use because a high degree of variation in the dissolution and rate of release of bromocriptine mesylate from the finished drug product, and problems in achieving acceptable product uniformity were found.

One formulation and process for the large scale preparation of bromocriptine mesylate tablets is described in Example 1. The process for preparing the tablets on an 80 kg batch scale involved geometrical mixing of the ingredients in several sub-batches followed by final mixing in a 5 ft$^3$ V-blender followed by discharge into a stainless steel container which was used to feed a 38-station tablet press.

For manufacturing process validation purposes, three 80 kg batches of tablets were prepared using the method described in Example 1. As described in Example 2, both the dissolution (drug release) properties and the tablet content uniformity were measured for samples of tablets from each of the batches. All of the batches showed acceptable drug release, where at least about 97% of the drug had been released at about 30 minutes as measured using the USP Apparatus Type 2 Paddle Method at 50 rpm in 500 mL of 0.1 N hydrochloric acid at 37° C. However, the batches did not show acceptable content uniformity as two of the three batches exhibited a relative standard deviation (RSD) bromocriptine content greater than the pass criteria. In addition, a trend was observed for all three batches in which the highest active ingredient content was found in tablets prepared towards the end of the compression run, which suggested that the non-uniformity might be accounted for by settling of the ingredients in the mixture after blending but before tablet compression was carried out.

A modified process was therefore developed and was carried out as described in Example 3. The tablets contain bromocriptine mesylate (0.945 mg/tablet) together with corn starch (9.00 mg/tablet) as a disintegrant, granular anhydrous citric acid (1.35 mg/tablet), anhydrous lactose (77.58 mg/tablet), colloidal silicon dioxide (0.45 mg/tablet) and magnesium stearate (0.675 mg/tablet). The tablets were prepared as described for the tablets of Example 1, except that the method for the final blending and tableting was modified. Based on the reasoning that the problem in achieving content uniformity when preparing a formulation as described in Example 1 was likely due to settling of ingredients after performing the final blending but before tableting, for example as a result of the transfer of blend from the blender to immediate storage containers prior to compression of the blended mixture, the method of Example 3 was modified to allow transfer of the blended mixture directly from the blending vessel to the tablet press for compression of the blended mixture. This was achieved by modifying the manufacturing process so that the final stage of blending was carried out in an in-bin hopper where the lubrication and final blending is performed. Following blending, the lubricated blend is transferred directly from the in-bin hopper to the tablet press using a valved transfer chute to avoid settling of the material prior to tablet compression.

Validation of the manufacturing method described in Example 3 for bromocriptine mesylate tablet manufacture was performed as described in Example 4. Three 80 kg batches of tablets were prepared using this method. Both the dissolution (drug release) properties and the tablet content uniformity were measured for samples of tablets from each of the batches. All of the batches showed acceptable drug release, with an average of at least about 95% of the drug released at about 30 minutes as measured using the USP Apparatus Type 2 Paddle Method at 50 rpm in 500 mL of 0.1 N hydrochloric acid at 37° C. In addition, all of the batches showed acceptable tablet content uniformity, with RSD values that were significantly lower than the RSD values quoted in Example 2 being observed. Therefore, a substantial improvement in tablet content uniformity was achieved by the modification to the process involving carrying out the blending in an in-bin hopper and transferring the blended material directly for tableting via a valved transfer chute.

Based on the results of Example 4, a manufacturing process carried out as described in Example 3 is preferred for manufacturing bromocriptine mesylate tablets suitable for treating type 2 diabetes to provide tablets with good content uniformity. Following blending of the formulation ingredients, compression of the mixture is carried out directly Although the method of Example 3 gave bromocriptine mesylate tablets with good content uniformity, it was unexpectedly found that tablets made using the method exhibited poor reproducibility of drug release.

The problem of achieving consistent, rapid drug release from a bromocriptine mesylate formulation prepared for improving glycemic control in the treatment of type 2 diabetes is illustrated by the data described in Example 5. Although the validation batches described in Example 4 all had shown an acceptable drug release profile (i.e., wherein an average of about 95% or greater of the drug release has been released at about 30 minutes), dissolution results obtained with further batches of bromocriptine mesylate tablets manufactured using the formulation and manufacturing process of Example 3 showed substantial variability in the percentage of drug released at 30 minutes (as determined using USP Apparatus Type 2 Paddle Method at 50 rpm in 500 mL of 0.1 N hydrochloric acid at 37° C.). Although certain batches had an acceptable release profile (i.e., about 90% or greater had been released at about 30 minutes), several batches had a significantly lower and unacceptable degree of release. See Table 7.

As described in Example 6, an extensive investigation was conducted to determine the cause of the observed variability. This investigation included an evaluation of the analytical method used to determine the amount of bromocriptine dissolved, a review of the raw materials, equipment, operators, batch records, and batch data, and the effect of variations in the blend time, tablet hardness, feeder speed, lactose particle size, reduced magnesium stearate concentration, removal of silicon dioxide, and reduced or increased corn starch concentration. In addition, batches of bromocriptine mesylate used in tablet batches having different release profiles were compared using differential scanning calorimetry to investigate whether a change in form of the bromocriptine might be responsible for the variable drug release. None of these investigations succeeded in identifying a reason for the variable drug release properties that were observed.

Ultimately, the possible role of the particle size of bromocriptine mesylate used in the manufacturing process was investigated. The bromocriptine mesylate used for the preparation of the tablets was prepared by a process in which the bromocriptine mesylate crystals were generated by addition of methanesulfonic acid at a late stage of the production process. Although this process produces high quality bromocriptine mesylate, it does not control the particle size distribution. From measurements of the particle size distributions of the bromocriptine mesylate batches used to prepare the various batches of tablets, it was found that the bromocriptine mesylate batches used to prepare the tablets had a variety of particle size distributions.

It was also found that there was a correlation between the particle size distribution and whether or not the tablets manufactured using various bromocriptine mesylate batches provided release of drug in the manner required for effectively improving glycemic control in the treatment of type 2 diabetes, as summarized in Table 9. In particular, it was found that preparing bromocriptine mesylate tablets from bromocriptine mesylate having a Dv90 of less than about 20 µm consistently provided a drug release profile in which about 90% or more of the bromocriptine mesylate had been released at about 30 minutes. In contrast, bromocriptine mesylate tablets prepared from bromocriptine mesylate having a Dv90 of more than about 20 µm failed to consistently provide a drug release profile in which at least 90% of the bromocriptine mesylate had been released at about 30 minutes. The correlation between bromocriptine mesylate particle size and dissolution is shown in graphical form in FIG. 1.

Figure 2:
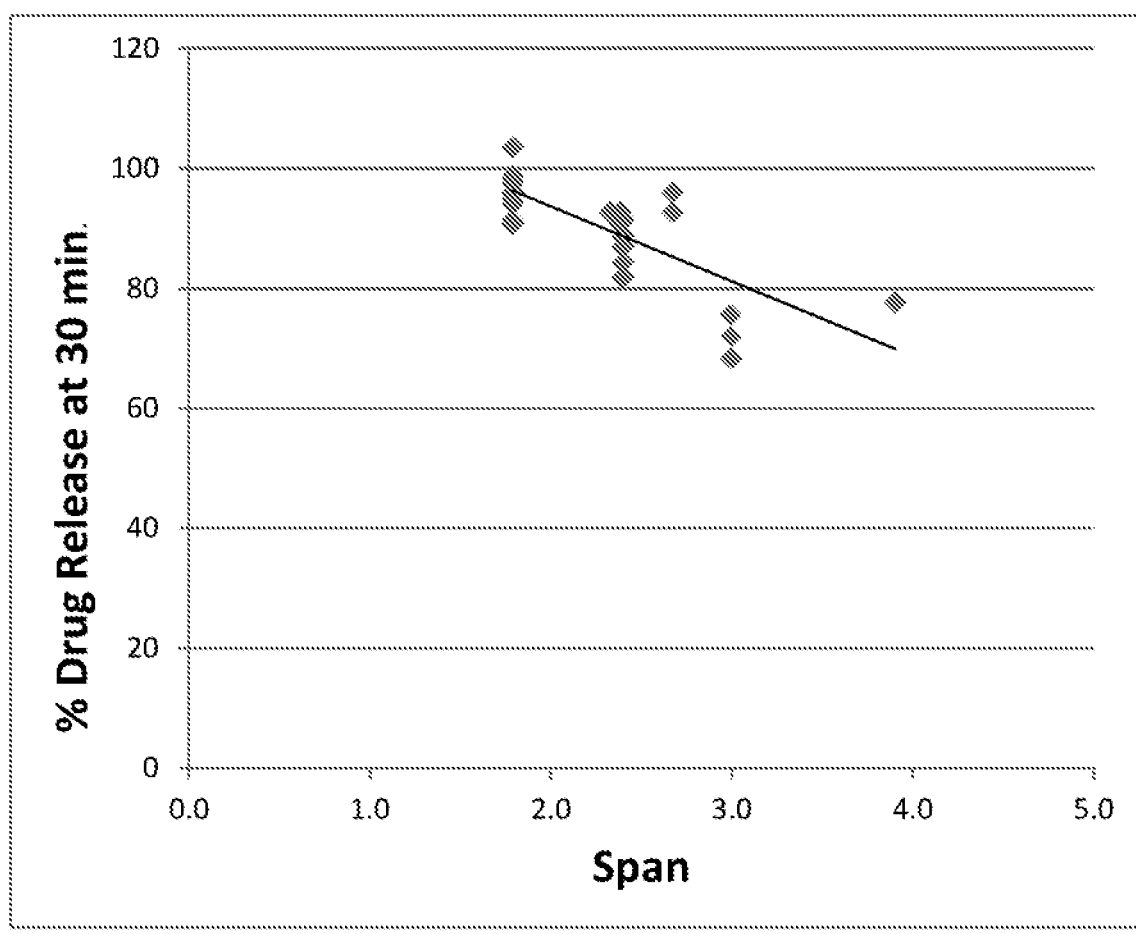
FIG. 2 is a plot showing the correlation between release at about 30 minutes for various batches of bromocriptine mesylate tablets and the span of the particle size distribution of the bromocriptine mesylate particles from which the batches were prepared.

It was also found that there was a correlation between the span of the volume-based particle size distribution and drug release. Preparing bromocriptine mesylate tablets from bromocriptine mesylate with a particle-size distribution having a span of less than about 2.0 consistently provided a drug release profile in which 90% or more of the drug had been released at about 30 minutes, whereas bromocriptine mesylate tablets prepared from bromocriptine mesylate having a volume-based particle distribution having a span of greater than about 2 did not consistently provide a drug release profile wherein at least about 90% of the drug had been release at about 30 minutes. The correlation between bromocriptine mesylate particle-size distribution span and dissolution is shown in graphical form in FIG. 2.

Based on the foregoing results, it has therefore been discovered that the manufacture of bromocriptine mesylate tables for improving glycemic control in patients with type 2 diabetes can be improved significantly by carefully controlling the size of the bromocriptine mesylate particles used in manufacturing the tablets. By controlling the particle size, tablets can be manufactured which consistently provide a release profile wherein about 90% or greater of the drug has been released at about 30 minutes thereby ensuring that the product is produced with a consistently acceptable potency and safety profile for improving glycemic control and treating type 2 diabetes. This is particularly useful when a manufacturing method is employed that achieves improved content uniformity by employing direct transfer of the bromocriptine formulation mixture for tableting after blending without allowing time for the ingredients to settle in the blended mixture Advantages include the ability to reproducibly produce drug product with a defined drug content and drug release profile to meet quality standards mandated by drug regulatory authorities such as the Food and Drug Administration.

Based on the foregoing studies, the inventors have found methods that, by using bromocriptine mesylate with controlled particle size as well as other methods described herein, bromocriptine mesylate tablets that are suitable for improving type 2 diabetes can be prepared with consistently good drug release properties as well as with good content uniformity.

One method that has been found useful is to control the particle size by use of micronized bromocriptine mesylate. In one aspect, it has been discovered that a superior bromocriptine mesylate formulation for improving glycemic control and treating type 2 diabetes can be prepared by using micronized bromocriptine mesylate for manufacturing bromocriptine mesylate tablets. The micronized bromocriptine mesylate may have a Dv90 of less than about 10 µm. In some embodiments, the micronized bromocriptine has a Dv90 of less than about 5 µm.

In some embodiments, the micronized bromocriptine mesylate has a Dv99 of less than about 15 µm. In some embodiments, the micronized bromocriptine mesylate has a Dv99 of less than about 10 µm.

In some embodiments, the micronized bromocriptine mesylate has a volume-based particle size distribution wherein not more than about 20% of the bromocriptine mesylate has a particle size of less than about 1 µm.

In some embodiments, the micronized bromocriptine mesylate has a volume-based particle size with a Dv99 of less than about 15 µm; a Dv90 of less than about 10 µm; and wherein not more than about 20% of the bromocriptine mesylate has a particle size of less than about 1 µm.

The bromocriptine mesylate tablet prepared using micronized bromocriptine is formulated to provide a dissolution profile such that, when tested in USP Apparatus Type 2 paddle method at 50 rpm in 500 mL of 0.1 N hydrochloric acid at about 37° C., the tablet has released at least about 80%, preferably at least about 90% of the bromocriptine mesylate at about 30 minutes. Preferably, the bromocriptine mesylate tablet provides a dissolution profile such that the tablet has released at least about 95% of the bromocriptine mesylate at about 30 minutes. In some embodiments, the bromocriptine mesylate tablet provides a dissolution profile such that the tablet has released at least about 80%, and preferably at least about 90%, of the bromocriptine mesylate at about 20 minutes.

Although the bromocriptine mesylate tablet is formulated to provide a dissolution profile such that, when tested in USP Apparatus Type 2 paddle method at 50 rpm in 500 mL of 0.1 N hydrochloric acid at about 37° C., the tablet has released at least about 80%, preferably about 90%, or most preferably about 95%, of the bromocriptine mesylate at about 30 minutes, extremely rapid release of bromocriptine mesylate from the formulation may not be desired, since a formulation that releases bromocriptine extremely rapidly may result in an undesired spike in in vivo drug levels and may not be suitable for treating type 2 diabetes, or give rise to side-effects. Therefore, in some embodiments, the bromocriptine mesylate tablet prepared using micronized bromocriptine mesylate is formulated to provide a dissolution profile such that, when tested in USP Apparatus Type 2 paddle method at 50 rpm in 500 mL of 0.1 N hydrochloric acid at about 37° C., not more than about 75%, not more than about 60%, or not more than about 50% of the bromocriptine mesylate has been released at about 7 minutes, and/or not more than about 90%, not more than about 85%, not more than about 80%, or, not more than about 75% of the bromocriptine mesylate has been released at about 10 minutes. The release profiles may be achieved by producing bromocriptine mesylate tablets using bromocriptine mesylate having a particular particle size distribution so that the finished drug product consistently provides a dissolution profile that is suitable for treatment of type 2 diabetes.

The bromocriptine mesylate tablet prepared using micronized bromocriptine mesylate is formulated to provide a pharmacokinetic profile wherein the time to maximum plasma concentration ($T_{max}$) following administration of six bromocriptine mesylate tablets, each providing a dose of about 0.8 mg of bromocriptine, is between about 30 and about 60 minutes, such as about 50 minutes, e.g. about 53 minutes, when the tablets are administered under fasting conditions, or between about 90 and about 120 minutes, when the tablets are administered under high fat fed conditions, to adult subjects.

The bromocriptine mesylate tablet may contain an amount of bromocriptine mesylate that provides a dose of at least about 0.8 mg of bromocriptine mesylate per tablet.

The formulations disclosed herein may further include citric acid. Citric acid may act as an antioxidant to improve the stability of the bromocriptine, but also may enhance bromocriptine absorption. Other antioxidants which may be used include, but are not limited to, vitamins A, C, E, beta-carotene, zinc, selenium, glutathione, coenzyme Q-10 and echinacea. The formulations disclosed herein may also include one or more disintegrating agent. Examples of suitable disintegrating agents include, but are not limited to, corn starch, sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. The formulations disclosed herein may also include one or more diluents. Examples of suitable diluents include, but are not limited to, lactose (e.g., monohydrate, spray-dried monohydrate, anhydrous and the like), mannitol, xylitol, dextrose, sucrose, sorbitol, microcrystalline cellulose, starch and dibasic calcium phosphate dihydrate. The formulations disclosed herein may also include one or more lubricants. Examples of suitable lubricants include, but are not limited to, magnesium stearate, colloidal silicon dioxide, calcium stearate, zinc stearate, stearic acid, talc, glyceryl behenate, polyethylene glycol, polyethylene oxide polymers, sodium lauryl sulfate, magnesium lauryl sulfate, sodium oleate, sodium stearyl fumarate, DL-leucine, colloidal silica, and others as known in the art. In some embodiments, the formulation used is prepared substantially as described in Example 9 using micronized bromocriptine mesylate.

Micronization provides for reduction of particle size to provide particles that are on the order of microns in diameter as measured by methods known to those of ordinary skill in the art, such as the volume distribution method. Methods of micronizing bromocriptine mesylate to afford formulations disclosed herein include those that are known to those of ordinary skill in the art and include, but are not limited to, milling, grinding, and the use of supercritical fluids. For example, one method of micronization (the "rapid expansion of supercritical solutions" or RESS method), material is dissolved in supercritical fluid under high temperature and pressure and the resulting solution is expanded through a nozzle to form small particles.

Micronization by jet milling is a method that can be used to produce particles in the lower micrometer range, and is the preferred method for micronizing bromocriptine mesylate. In brief, the raw material with a maximum size of about 1 to 2 mm is introduced into the milling chamber via a gas stream. Within the milling chamber a circular gas stream accelerates the particles which are micronized by collision with each other or with the wall of the chamber. The ground particles are removed from the milling chamber by the gas stream, while the larger ones stay inside due to centrifugal forces. In the preferred process for micronizing bromocriptine, micronization is performed using a jet mill under a nitrogen atmosphere at a controlled temperature of about 0° C.

Figure 3A:
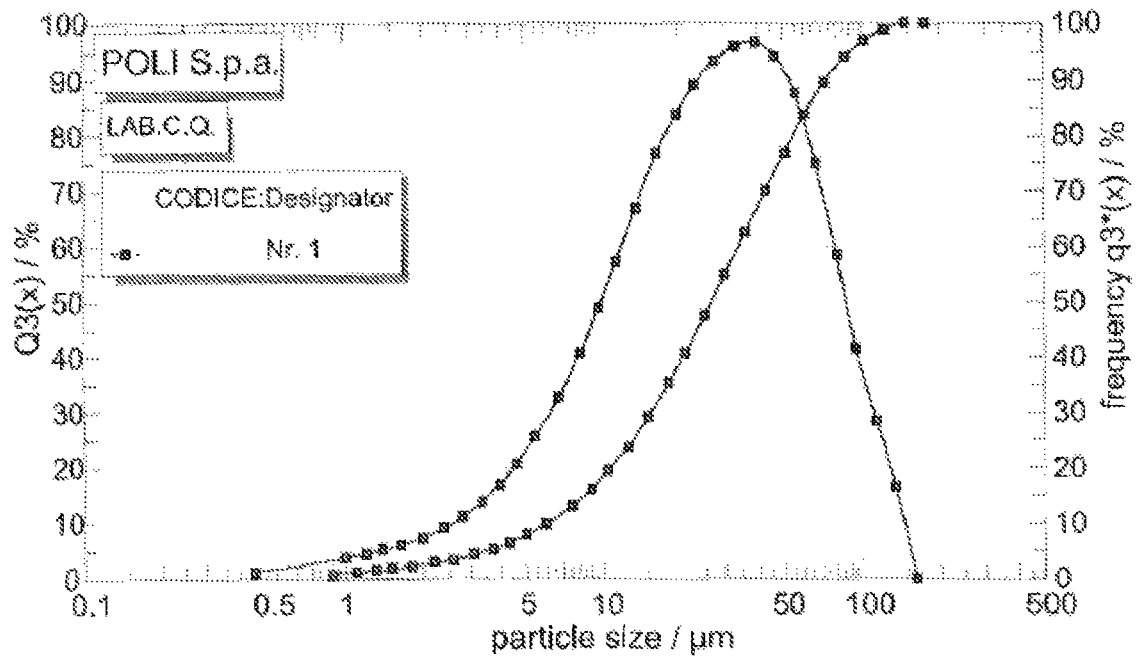
FIG. 3A shows the volume-based particle size distribution measured for a batch of bromocriptine mesylate particles before micronization.
Figure 3B:
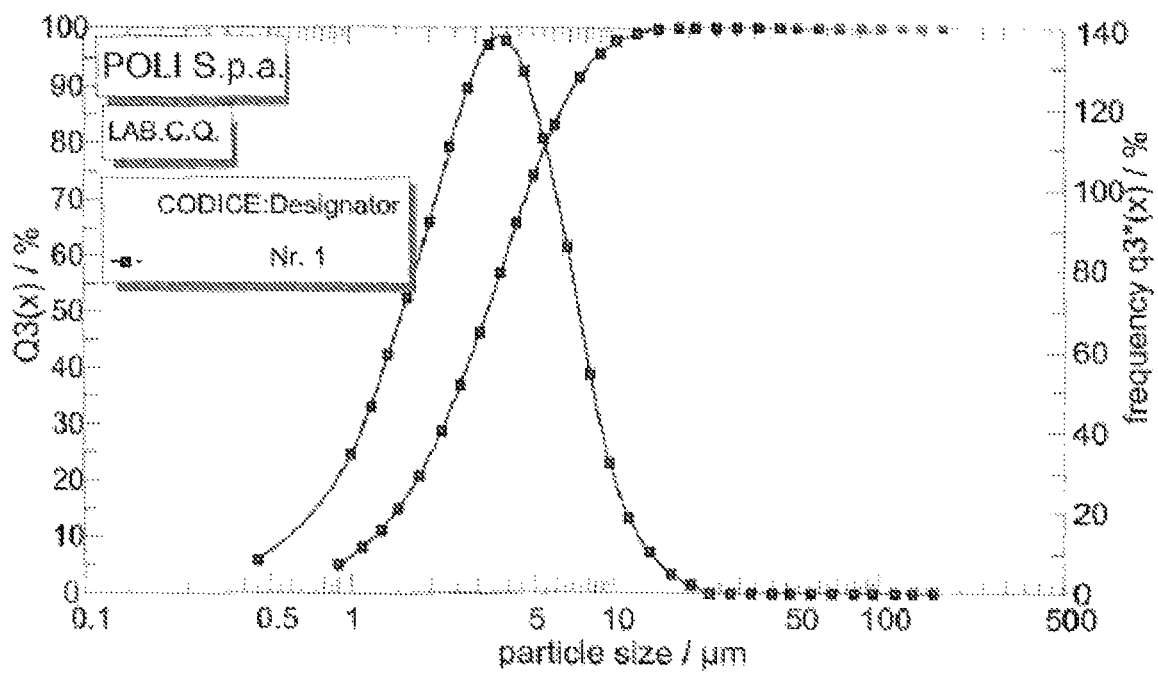
FIG. 3B shows the volume-based particle size distribution measured for a batch of bromocriptine mesylate particles after micronization.

Example 7 describes the preparation of batches of micronized bromocriptine mesylate and characterization of their properties. As shown in Table 10, micronization produced bromocriptine material with similar particle size distributions after micronization even when bromocriptine mesylate batches with rather different materials were used as the starting material. Exemplary particle size distributions for a batch of bromocriptine mesylate before and after micronization are shown in FIGS. 3A and 3B.

Example 8 illustrates the improved and consistent drug release profiles that can be achieved by employing micronized bromocriptine mesylate to prepare bromocriptine mesylate tablets. Tablets prepared with micronized bromocriptine mesylate had significantly improved drug release (98% of the bromocriptine released by 30 minutes) compared to tablets prepared from the same batch of bromocriptine mesylate without micronization (which released only 69% of the bromocriptine mesylate at 30 minutes).

Figure 4:
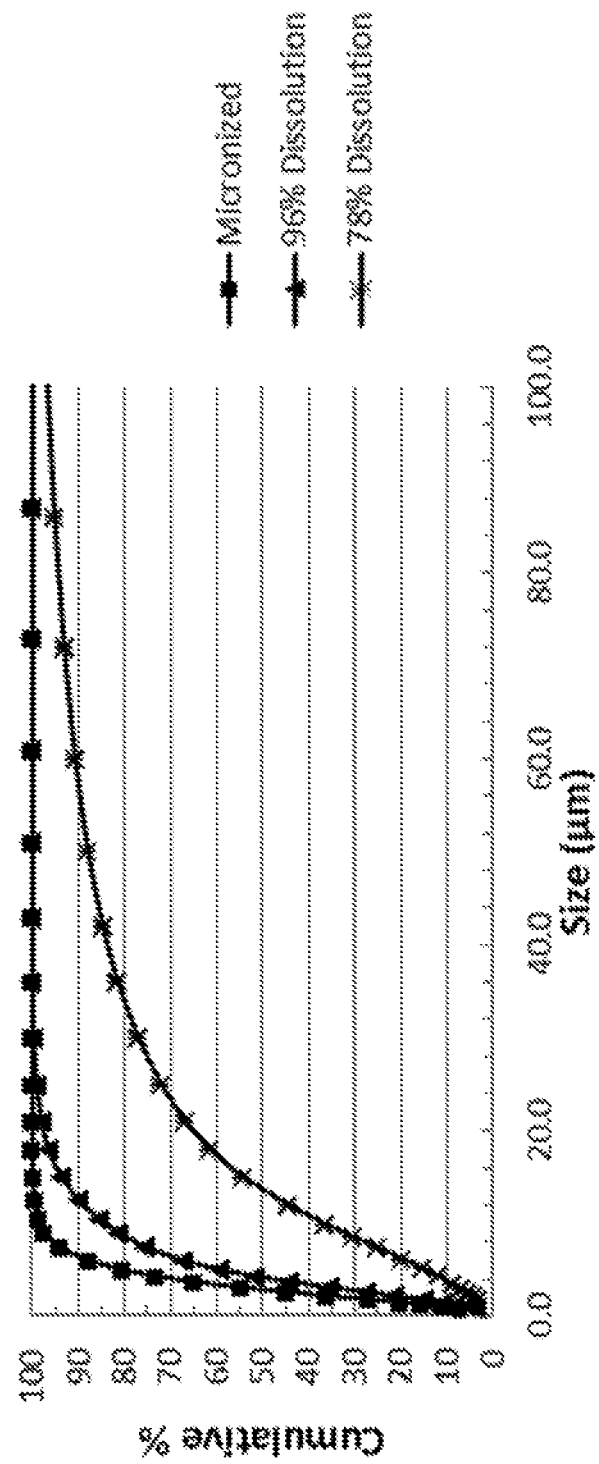
FIG. 4 shows the cumulative volume-based particle size distribution for a batch of micronized bromocriptine mesylate particles compared with batches of bromocriptine mesylate used in tablets which released about 96% of the bromocriptine at about 30 minutes (as compared to batches that released about 78% of the bromocriptine at about 30 minutes.

The relationship between particle size distribution and drug release/dissolution for bromocriptine mesylate is further illustrated in FIG. 4. FIG. 4 shows plots of the cumulative volume-based particle size distribution for three batches of bromocriptine mesylate: a batch of bromocriptine mesylate which was used in a bromocriptine mesylate tablet formulation (prepared as described in Example 3) which had released 96% of the bromocriptine mesylate at 30 minutes when tested in USP Apparatus Type 2 Paddle Method at 50 rpm in 500 mL of 0.1 N hydrochloric acid at about 37° C.; a batch of bromocriptine mesylate which was used in a bromocriptine mesylate tablet formulation (prepared as described in Example 3) which had released about 78% of the bromocriptine mesylate at 30 minutes when tested in USP Apparatus Type 2 Paddle Method at 50 rpm in 500 mL of 0.1 N hydrochloric acid at about 37° C.; and a batch of micronized of bromocriptine mesylate.

In another aspect, it has been discovered that a method of manufacturing a bromocriptine mesylate formulation for improving glycemic control in treating type 2 diabetes using a manufacturing process that selectively controls bromocriptine mesylate particle size, for example by employing particle size measurement and/or processing bromocriptine mesylate to reduce the particle size, to prepare bromocriptine mesylate tablets that, when tested in USP Apparatus Type 2 Paddle Method at 50 rpm in 500 mL of 0.1 N hydrochloric acid at about 37° C. consistently provide a drug release profile wherein at least 90%, and preferably at least 95%, of the drug is released within about 30 minutes. The result is achieved by controlling the particle size distribution of the bromocriptine mesylate to be within the particle size range that has been found to result in bromocriptine tablets having the desired drug release profile.

In some embodiments, particle size measurement is employed to select bromocriptine mesylate having a particle size distribution that consistently provides a drug release profile wherein at least about 80%, or preferably least about 90%, or at least about 95%, of the drug is released within about 30 minutes. The method comprises determining that the bromocriptine mesylate has a particle size distribution which provides the requisite drug release profile and subsequently blending the bromocriptine mesylate of determined particle size distribution with excipients to form a mixture wherein the bromocriptine mesylate is substantially evenly distributed in the mixture, and then compressing the mixture to form one or more tablets. The tablet may comprise an amount of bromocriptine mesylate that provides a dose of at least about 0.8 mg of bromocriptine. The tablet may provide a dissolution profile, when tested in USP Apparatus Type 2 Paddle Method at 50 rpm in 500 mL of 0.1 N hydrochloric acid at about 37° C., wherein at least about 80%, or preferably at least about 90% or about 95%, of the bromocriptine mesylate has been released at about 30 minutes. The method preferably comprises determining that the bromocriptine mesylate has a Dv90 of less than about 20 µm. It is not essential to determine the volume-based particle size distribution per se since other methods of measuring the particle size distribution (such as number-based or mass-based methods) could be used. The method should, however, comprise determining that the bromocriptine mesylate particle size distribution is equivalent to a Dv90 of less than about 20 µm.

In some embodiments, particle size measurement is employed to select bromocriptine mesylate having a particle size distribution that consistently provides a drug release profile wherein at least about 80%, and preferably at least about 90%, of the bromocriptine mesylate has been released at about 20 minutes when tested in USP Apparatus Type 2 Paddle Method at 50 rpm in 500 mL of 0.1 N hydrochloric acid at about 37° C.

In some embodiments, particle size measurement is employed to select bromocriptine mesylate having a particle size distribution that consistently provides a drug release profile wherein not more than about 75%, not more than about 60%, or not more than about 50% of the bromocriptine mesylate has been released at about 7 minutes when tested in USP Apparatus Type 2 Paddle Method at 50 rpm in 500 mL of 0.1 N hydrochloric acid at about 37° C., and/or not more than about 90%, not more than about 85%, not more than about 80%, or not more than about 75%, of the bromocriptine mesylate has been released at about 10 minutes when tested in USP Apparatus Type 2 Paddle Method at 50 rpm in 500 mL of 0.1 N hydrochloric acid at about 37° C.

In some embodiments, particle size measurement is employed to select bromocriptine mesylate having a particle size distribution that consistently provides a tablet with a pharmacokinetic profile wherein the time to maximum plasma concentration ($T_{max}$) following administration of six bromocriptine mesylate tablets, each providing a dose of about 0.8 mg of bromocriptine, is between about 30 and about 60 minutes, such as about 50 minutes, e.g. about 53 minutes, when the tablets are administered under fasting conditions, or between about 90 and about 120 minutes, when the tablets are administered under high fat fed conditions, to adult subjects.

The size of the bromocriptine mesylate particles and the particle size distribution may be determined by any of several methods. Methods useful for analyzing particle size within the range of about 10 nm to 100 µm, include, but are not limited to: laser diffraction particle size analysis, mechanical sieving, optical microscopy, ultracentrifugation, sedimentation, air permeability, electron microscopy, scanning electron microscopy and Coulter Counter techniques. Methods for determining particle size are described, for example, in Martin et al., Physical Pharmacy, 3rd Ed., Lea & Febiger, Philadelphia (1983); and Merkus et al., Particle Size Measurements, Fundamentals, Practice, Quality, Springer (2009).

Optical microscopy is useful for particle size measurement in the range of about 0.2 µm to about 100 µm. For optical microscopy, an emulsion or suspension, diluted or undiluted, is mounted on a slide or ruled cell. The microscope eyepiece is fitted with a micrometer by which the size of the particles may be estimated.

Mechanical sieving uses a series of standard sieves calibrated by the National Bureau of Standards. Mechanical sieves may be used for screening material as fine as 44 µm (No. 325 sieve). Sieves manufactured by photo-etching and electroforming are available with apertures from 90 µm to 5 µm.

Measurements obtained using laser diffraction are preferred. These techniques operate on the principle that different sizes of particles produce a different diffraction pattern, which depends on the size of the particle. In laser particle size analysis, laser light which has been passed through a sample of particles is scattered onto a Fourier lens that focuses the scattered light onto a detector array. An inversion algorithm is used to infer the particle size distribution from the collected diffracted light data.

Laser diffraction measurement of particle size can use a dry method (wherein a suspension of the compound/salt in an airflow crosses the laser beam) or a wet method (wherein a suspension of the compound/salt in a liquid dispersing medium, such as isooctane or about 0.05% lecithin in isooctane or (e.g., if compound is soluble in isooctane) 0.1% Tween 80 in water, crosses the laser beam. With laser diffraction, particle size is preferably calculated using the Fraunhofer calculation; and/or preferably a Sympatec or Malvern Mastersizer apparatus is used for measurement.

The particle size distribution ranges defined herein are based upon measurements made using technology and instruments using laser particle size analysis using the instruments and methods developed by SYMPATEC GmbH, in particular Sympatec HELOS which can provide particle size analysis of dry and wet samples, i.e., of powders, suspensions, emulsions or sprays and is built to the specifications of ISO 13320 "Particle size analysis—laser diffraction methods."

Notwithstanding expected variability in the precise values for particle size and particle size distribution measurements obtained using different instruments and analytical methods, the claims are not intended to be limited by or to a particular method of particle-size measurement or analysis.

In some embodiments, the particle size of the bromocriptine mesylate used to make bromocriptine mesylate tablet is controlled by including in the manufacturing process a step of processing bromocriptine mesylate to reduce its average particle size so as to provide bromocriptine mesylate that has a Dv90 of less than about 20 µm. The bromocriptine mesylate used as a starting material may have a Dv90 of more than about 20 µm and the processing may include reducing the size of bromocriptine mesylate particles (e.g., by grinding, milling, or micronization) or sieving to remove larger particles. After the bromocriptine mesylate particle size has been reduced, the bromocriptine mesylate is blended with excipients to form a mixture wherein the bromocriptine mesylate is evenly distributed in the mixture, and then the mixture is compressed to form one or more tablets. The tablet may comprise an amount of bromocriptine mesylate that provides a dose of at least about 0.8 mg of bromocriptine. The tablet may provide a dissolution profile, when tested in USP Apparatus Type 2 Paddle Method at 50 rpm in 500 mL of 0.1 N hydrochloric acid at about 37° C., wherein at least about 80%, preferably at least about 90%, or at least about 95%, of the bromocriptine mesylate has been released at about 30 minutes. In some embodiments, the tablet may provide a dissolution profile, when tested in USP Apparatus Type 2 Paddle Method at 50 rpm in 500 mL of 0.1 N hydrochloric acid at about 37° C., wherein at least about 80%, or at least about 90%, of the bromocriptine mesylate has been released at about 30 minutes. In some embodiments, the tablet may provide a dissolution profile, when tested in USP Apparatus Type 2 Paddle Method at 50 rpm in 500 mL of 0.1 N hydrochloric acid at about 37° C., wherein not more than about 75%, not more than about 60%, or not more than about 50% of the bromocriptine mesylate has been released at about 7 minutes, and/or not more than about 90%, not more than about 85%, not more than about 80% or, not more than about 75% of the bromocriptine mesylate has been released at about 10 minutes.

In some embodiments, the tablet may have a pharmacokinetic profile wherein the time to maximum plasma concentration ($T_{max}$) following administration of six bromocriptine mesylate tablets, each providing a dose of about 0.8 mg of bromocriptine, is between about 30 and about 60 minutes, such as about 50 minutes, e.g. about 53 minutes, when the tablets are administered under fasting conditions, or between about 90 and about 120 minutes, when the tablets are administered under high fat fed conditions, to adult subjects.

In some embodiments of the methods described above, the bromocriptine mesylate used for manufacturing the tablets is selected or processed to have a Dv90 of less than about 20 μm, less than about 18 μm, less than about 16 μm, less than about 15 μm, less than about 10 μm, or less than about 5 μm. In some embodiments, the bromocriptine mesylate used for manufacturing the tablets is selected or processed to have a Dv50 of less than about 10 μm, less than about 8 μm, less than about 7 μm, or less than about 5 μm. In some embodiments, the bromocriptine mesylate used for manufacturing the tablets is selected or processed to have a Dv10 of less than about 5 μm, less than about 3 μm, or less than about 2 μm. In some embodiments of the methods described above, the bromocriptine mesylate used for manufacturing the tablets is selected or processed to have a volume-based particle size distribution such that not more than about 40%, not more than about 20%, not more than 10% or not more than about 5% of the bromocriptine mesylate has a particle size of less than about 1 μm.

In some embodiments, the bromocriptine mesylate used for manufacturing the tablets is selected or processed to have a particle size such that the particle size distribution has a Dv90 of about 20 μm or lower, a Dv50 of about 10 μm or lower and a Dv10 of about 5 μm or lower. In some embodiments, the bromocriptine mesylate used for manufacturing the tablets is selected or processed to have a particle size such that the particle size distribution has a Dv90 of about 15 μm or lower, a Dv50 of about 8 μm or lower and a Dv10 of about 3 μm or lower. In some embodiments, the bromocriptine mesylate used for manufacturing the tablets is selected or processed to have a particle size such that the particle size distribution has a Dv90 of about 10 μm or lower, a Dv50 of about 5 μm or lower and a Dv10 of about 3 μm or lower. In some embodiments, the bromocriptine mesylate used for manufacturing the tablets is selected or processed to have a particle size such that the particle size distribution has a Dv90 of about 8 μm or lower, a Dv50 of about 5 μm or lower and a Dv10 of about 3 μm or lower. In some embodiments, the bromocriptine mesylate used for manufacturing the tablets is selected or processed to have a particle size such that the particle size distribution has a Dv90 of about 5 μm or lower, a Dv50 of about 3 μm or lower and a Dv10 of about 1 μm or lower.

In some embodiments bromocriptine mesylate used for manufacturing the tablets is selected or processed to have a volume-based particle size such that the particle size span is about 3 or lower, about 2.5 or lower, or about 2 or lower.

In addition, in some embodiments, particle size measurement as described above and processing to reduce the average particle size may be combined to provide additional control in preparing bromocriptine mesylate tablets. For example, following processing to reduce the average particle size, particle size measurement may be performed to ensure that the particle size distribution is within a range that provides consistent drug release. In addition, micronization may be employed as a technique to reduce the particle size to prepare a bromocriptine mesylate tablet that comprises micronized bromocriptine as described in greater detail above.

The bromocriptine mesylate tablet prepared by the methods described herein may be formulated with citric acid. The formulation may also include a disintegrating agent. In some embodiments, the disintegrating agent is corn starch. In some embodiments, the formulation further comprises lactose, colloidal silicon dioxide and magnesium stearate. In some embodiments, the bromocriptine mesylate tablets are prepared substantially as described in Example 1.

As discussed above, the data provided in Example 8 (Table 11) illustrate the effect of processing bromocriptine mesylate to improve and provide consistent dissolution properties and show that a significantly greater degree of drug release (at 30 minutes) was obtained from tablets manufactured using micronized bromocriptine mesylate as compared to the same batch of bromocriptine mesylate without micronization. The data also demonstrate the effectiveness of controlling particle size and employing processing to reduce the bromocriptine mesylate particle size for consistently producing a drug product with superior release properties.

The bromocriptine mesylate tablets described herein, and bromocriptine mesylate tablets prepared by the methods herein, may be used to treat type 2 diabetes by improving glycemic control in an individual with type 2 diabetes. The tablet is administered within about two hours after waking in the morning with food. The initial dose is about 0.8 mg of bromocriptine daily, which is increased weekly by one tablet until a maximal tolerated daily dose of about 1.6 to about 4.8 mg (2 to 6 tablets) is achieved.

EXAMPLES

The inventors' discoveries are illustrated by the following examples, which are not intended to limit the scope of the claims. Other variations or embodiments of the invention will also be apparent to one of ordinary skill in the art from the above descriptions and the following Examples.

Example 1. Preparation of a Bromocriptine Mesylate Tablet Formulation

Bromocriptine mesylate tablets are prepared having the ingredients listed in Table 1 below.

TABLE 1

Bromocriptine Mesylate Tablet Formulation.

| Ingredient | Quantity (mg/tablet) | Quantity (kg/batch) |
| --- | --- | --- |
| Bromocriptine mesylate USP | 0.945 | 0.84 |
| Corn starch NF | 9.00 | 8.00 |
| Granular anhydrous citric acid USP | 1.35 | 1.20 |

TABLE 1-continued

Bromocriptine Mesylate Tablet Formulation.

| Ingredient | Quantity (mg/tablet) | Quantity (kg/batch) |
|---|---|---|
| Anhydrous lactose NF | 77.58 | 69.00 |
| Colloidal silicon dioxide NF | 0.45 | 0.40 |
| Magnesium Stearate NF | 0.675 | 0.60 |
| Total Weight | 90.0 | 80.0 |

The tablets were prepared by geometrical mixing via trituration of bromocriptine mesylate (Euticals S.p.a., Milan) with corn starch as four triturations in a PK Blend-Master™ V-Blender. Sequentially, two sub-loads of granular anhydrous citric acid and corn starch were mixed in a PK BlendMaster™. These two sub-loads were each divided into two equal sub-loads, yielding a total of four sub-loads. Each of the four bromocriptine mesylate triturations was then mixed with adjusted amounts of anhydrous lactose, corn starch and one citric acid/starch corn sub-load in a Fielder PMA 65 mixer to form four premixes [A-D]. A 2.0 kg quantity was removed after Premix A for mixing in a PK BlendMaster™ with colloidal silicon dioxide and magnesium stearate to form a lubricant premix. The four premixes were then loaded in sequential order, with the lubricant premix loaded in between premixes B and C, into a 5 ft³ V-blender where lubrication/final blending was performed. The lubricated blend was then discharged into a stainless steel container which was used to feed a 38-station HATA tablet press. The tablets were compressed using the tablet press.

Example 2. Validation Studies for Tablets Prepared According to Example 1

Three batches were prepared using the method described in Example 1 to validate the manufacturing method.

Drug release profiles for samples of the tablets were measured using the USP Apparatus Type 2 Paddle Method at 50 rpm in 500 mL of 0.1 N hydrochloric acid at 37° C. Table 2 below shows the drug release profiles obtained for tablets from each batch.

TABLE 2

Drug Release from Three Batches of Bromocriptine Mesylate Tablets Prepared as Described in Example 1.

| Batch No. | Time (minutes) | Average % Release (n = 12) |
|---|---|---|
| 1 | 10 | 78 |
|   | 20 | 96 |
|   | 30 | 99 |
|   | 40 | 100 |
| 2 | 10 | 72 |
|   | 20 | 91 |
|   | 30 | 97 |
|   | 40 | 98 |
| 3 | 10 | 81 |
|   | 20 | 95 |
|   | 30 | 100 |
|   | 40 | 101 |

In addition, blend uniformity and tablet content uniformity were assessed.

Blend uniformity was assessed by assaying the content of the powdered formulation at ten locations in the blender following final blending but before tableting. All of the batches met the criteria for blend uniformity.

Tablet content uniformity was evaluated on a sample of 60 tablets from each batch. The tablets were assayed to assess, inter alia, the amount of bromocriptine present in the tablet relative to the label amount of 0.8 mg of bromocriptine. In addition, the mean and relative standard deviation (RSD) bromocriptine mesylate content was calculated for each batch. The content uniformity results obtained are summarized in Table 3. The tablet content uniformity requirements were not met for batches 2 and 3. In addition, a trend was observed for all three batches in which the highest active ingredient content was found in tablets prepared towards the end of the compression run.

TABLE 3

Content Uniformity Evaluation for Three Batches of Bromocriptine Mesylate Tablets Prepared as Described in Example 1 (n = 60 tablets for each batch).

| Batch No. | Bromocriptine Content (% of label) Mean | Range | RSD | RSD Pass Criterion[†] | Pass/Fail |
|---|---|---|---|---|---|
| 1 | 101.5 | 95.4-108.9 | 3.13 | 4.52 | Pass |
| 2 | 103.0 | 96.7-113.2 | 4.03 | 4.01 | Fail |
| 3 | 100.5 | 92.2-113.1 | 5.05 | 4.85 | Fail |

[†]The RSD pass criteria vary according to the bromocriptine content and are calculated using Bergum's method. Meeting the criterion provides 90% assurance that at least 95% of future samples from the same population would pass the USP content uniformity test Example 3. Modified Procedure for the Preparation of a Bromocriptine Mesylate Tablet Formulation Bromocriptine mesylate tablets were prepared having the ingredients listed in Table 4 below.

TABLE 4

Bromocriptine Mesylate Tablet Formulation.

| Ingredient | Quantity (mg/tablet) | Quantity (kg/batch) |
|---|---|---|
| Bromocriptine mesylate USP | 0.945 | 0.84 |
| Corn starch NF | 9.00 | 8.00 |
| Granular anhydrous citric acid USP | 1.35 | 1.20 |
| Anhydrous lactose NF | 77.58 | 69.00 |
| Colloidal silicon dioxide NF | 0.45 | 0.40 |
| Magnesium Stearate NF | 0.675 | 0.60 |
| Total Weight | 90.0 | 80.0 |

The tablets were prepared by geometrical mixing via trituration of bromocriptine mesylate (Euticals S.p.a., Milan) with corn starch as four triturations in a PK Blend-Master™ V-Blender. Sequentially, two sub-loads of granular anhydrous citric acid and corn starch were mixed in a PK BlendMaster™. These two sub-loads were each divided into two equal sub-loads, yielding a total of four sub-loads. Each of the four bromocriptine mesylate triturations was then mixed with adjusted amounts of anhydrous lactose, corn starch and one citric acid/starch corn sub-load in a Fielder PMA 65 mixer to form four premixes [A-D]. A 2.0 kg quantity is removed after Premix A for mixing in a PK BlendMaster™ with colloidal silicon dioxide and magnesium stearate to form a lubricant premix. The four premixes were then loaded in sequential order, with the lubricant premix loaded in between premixes B and C, into an 8 ft³ in-bin hopper; where lubrication/final blending was performed. The lubricated blend was then transferred from the in-bin hopper to a tablet press using a valved transfer chute, and then compressed using a 38-station Hata tablet press.

Example 4. Validation Studies for Tablets Prepared According to Example 3

To validate the manufacturing method, three batches were prepared using the method described in Example 3.

Drug release profiles for samples of the tablets were measured using the USP Apparatus Type 2 Paddle Method at 50 rpm in 500 mL of 0.1 N hydrochloric acid at 37° C. Table 5 below shows the drug release profiles obtained for tablets from each batch.

TABLE 5

Drug Release from Three Batches of Bromocriptine Mesylate Tablets Prepared as Described in Example 3.

| Batch No. | Time (minutes) | Average % Release (n = 12) |
|---|---|---|
| 1 | 10 | 91 |
|   | 20 | 101 |
|   | 30 | 104 |
|   | 40 | 103 |
| 2 | 10 | 84 |
|   | 20 | 100 |
|   | 30 | 103 |
|   | 40 | 104 |
| 3 | 10 | 83 |
|   | 20 | 95 |
|   | 30 | 97 |
|   | 40 | 98 |

In addition, blend uniformity and tablet content uniformity were assessed.

Blend uniformity was assessed by assaying the content of the powdered formulation at ten locations in the blender following final blending but before tableting. All of the batches met the criteria for blend uniformity.

Tablet content uniformity was evaluated on a sample of 60 tablets from each batch. The tablets were assayed to assess, inter alia, the amount of bromocriptine present in the tablet relative to the label amount of 0.8 mg of bromocriptine. In addition, the mean and relative standard deviation (RSD) bromocriptine mesylate content was calculated for each batch. The content uniformity results obtained are summarized in Table 6. In this case all three batches met the tablet content uniformity requirements, with RSD values that were significantly lower than the RSD values quoted in Example 2 being observed.

TABLE 6

Content Uniformity Evaluation for Three Batches of Bromocriptine Mesylate Tablets Prepared as Described in Example 4 (n = 60 tablets for each batch).

| Batch No. | Bromocriptine Content (% of label) | | | RSD Pass | |
|---|---|---|---|---|---|
|  | Mean | Range | RSD | Criterion† | Pass/Fail |
| 1 | 102.5 | 98.6-110.4 | 1.83 | 4.18 | Pass |
| 2 | 101.5 | 96.9-107.0 | 2.24 | 4.52 | Pass |
| 3 | 100.8 | 95.7-105.9 | 1.83 | 4.75 | Pass |

†The RSD pass criteria vary according to the bromocriptine content and are calculated using Bergum's method. Meeting the criterion provides 90% assurance that at least 95% of future samples from the same population would pass the USP content uniformity test Example 5. Evaluation of Drug Release from Bromocriptine Mesylate Tablet Preparations Over a period of time, a number of batches of bromocriptine mesylate tablets were prepared by methods substantially similar to the method described in Example 1 using micronized bromocriptine mesylate purchased from Euticals, S.p.a. Drug release from each batch of tablets was measured using USP Apparatus Type 2 Paddle Method at 50 rpm in 500 mL of 0.1 N hydrochloric acid at 37° C. at 30 minutes. The result of the drug release measurements, showing the percentage of drug released at about 30 minutes for each batch (entries 2, 3, 4, 5, 6, 16, 17, 20 and 22 are for single tablet batches, other entries represent data from multiple tablet batches) is summarized in Table 7 below.

TABLE 7

Dissolution Results Showing Percentage of Bromocriptine Mesylate Released at 30 Minutes From Different Batches of Bromocriptine Mesylate Tablets Prepared by Methods Substantially Similar to Example 1.

| Table Entry | Average Percentage Released at about 30 minutes (n = 6 to 24) |
|---|---|
| 1 | 96 |
| 2 | 93 |
| 3 | 93 |
| 4 | 93 |
| 5 | 91 |
| 6 | 91 |
| 7 | 94 |
| 8 | 95 |
| 9 | 96 |
| 10 | 97 |
| 11 | 98 |
| 12 | 98 |
| 13 | 99 |
| 14 | 104 |
| 15 | 89 |
| 16 | 91 |
| 17 | 91 |
| 18 | 92 |
| 19 | 92 |
| 20 | 87 |
| 21 | 87 |
| 22 | 87 |
| 23 | 89 |
| 24 | 78 |
| 25 | 89 |
| 26 | 82 |
| 27 | 84 |
| 28 | 68 |
| 29 | 72 |
| 30 | 76 |

Example 6. Investigation of the Cause of Variable Drug Release from Bromocriptine Mesylate Tablet Preparations An investigation was conducted into potential reasons for the variable drug release from different bromocriptine mesylate tablet preparations. The investigation covered analytical as well as manufacturing sources for the unexpected drug release results.

A number of variables in the HPLC analytical method used to measure the extent of drug release were investigated. Although it was found that minor improvements to reduce variability could be achieved, for example by using low actinic glassware, a chilled HPLC autosampler, and disposable plastic syringes, the variability could not be attributed to laboratory causes alone.

Investigation of the manufacturing process included numerous aspects of the production process, including the raw materials, equipment, operators, batch records, and batch data without identifying a root cause. As a result, smaller scale studies were designed to evaluate formulation variables and key operational variables of the production process. A summary of these studies and results obtained are provided in Table 8.

TABLE 8

Summary of Process Investigations Conducted to Investigate the Cause of Variable Drug Release from Bromocriptine Mesylate Tablet Preparations.

| Study Description | Dissolution Results |
|---|---|
| Low lubrication blend time | Comparable to Control |
| High lubrication blend time | Comparable to Control |
| Low tablet hardness | Comparable to Control |
| High tablet hardness | Comparable to Control |
| Low feeder speed | Comparable to Control |
| High feeder speed | Comparable to Control |
| Small particle size lactose | Comparable to Control |
| Reduced magnesium stearate concentration | Comparable to Control |
| Removal of silicon dioxide | Comparable to Control |
| Reduced corn starch concentration | Comparable to Control |
| Increased corn starch concentration | Comparable to Control |

Finally, the possible role of the particle size of bromocriptine mesylate used in the manufacturing process was investigated. The volume-based particle size distribution for the bromocriptine mesylate used in preparing the tablet batches was measured by laser diffractometry using a Sympatec HELOS Laser Diffractometer. The results are shown in Table 9, which lists the bromocriptine particle size distribution that was determined for the various batches of bromocriptine mesylate and the percentage drug that was released by 30 minutes determined for each of the batches.

TABLE 9

Dissolution Results Showing the Relationship Between the Percentage of Bromocriptine Mesylate Released at 30 Minutes Batches of Bromocriptine Mesylate Tablets and the Particle Size Distributions of the Bromocriptine Mesylate Used for Tablet Preparation.

| Table Entry | Dv10 | Dv50 | Dv90 | Span | Average Percentage Released at about 30 minutes (n = 6 to 24) |
|---|---|---|---|---|---|
| 1 | 1.5 | 4.2 | 12.6 | 2.7 | 96 |
| 2 | 1.5 | 4.2 | 12.6 | 2.7 | 93 |
| 3 | 1.8 | 5.3 | 14.4 | 2.4 | 93 |
| 4 | 1.6 | 4.6 | 12.3 | 2.3 | 93 |
| 5 | 1.8 | 5.3 | 14.4 | 2.4 | 91 |
| 6 | 2.4 | 7.2 | 15.3 | 1.8 | 91 |
| 7 | 2.4 | 7.2 | 15.3 | 1.8 | 94 |
| 8 | 2.4 | 7.2 | 15.3 | 1.8 | 95 |
| 9 | 2.4 | 7.2 | 15.3 | 1.8 | 96 |
| 10 | 2.4 | 7.2 | 15.3 | 1.8 | 97 |
| 11 | 2.4 | 7.2 | 15.3 | 1.8 | 98 |
| 12 | 2.4 | 7.2 | 15.3 | 1.8 | 98 |
| 13 | 2.4 | 7.2 | 15.3 | 1.8 | 99 |
| 14 | 2.4 | 7.2 | 15.3 | 1.8 | 104 |
| 15 | 3.1 | 10.4 | 28.1 | 2.4 | 89 |
| 16 | 3.1 | 10.4 | 28.1 | 2.4 | 91 |
| 17 | 2.4 | 7.2 | 15.3 | 1.8 | 91 |
| 18 | 3.1 | 10.4 | 28.1 | 2.4 | 92 |
| 19 | 3.1 | 10.4 | 28.1 | 2.4 | 92 |
| 20 | 3.1 | 10.4 | 28.1 | 2.4 | 87 |
| 21 | 3.1 | 10.4 | 28.1 | 2.4 | 87 |
| 22 | 3.1 | 10.4 | 28.1 | 2.4 | 87 |
| 23 | 3.1 | 10.4 | 28.1 | 2.4 | 89 |
| 24 | 3.9 | 13.7 | 57.4 | 3.9 | 78 |
| 25 | 3.1 | 10.4 | 28.1 | 2.4 | 89 |
| 26 | 3.1 | 10.4 | 28.1 | 2.4 | 82 |
| 27 | 3.1 | 10.4 | 28.1 | 2.4 | 84 |
| 28 | 2.3 | 7.9 | 25.8 | 3.0 | 68 |
| 29 | 2.3 | 7.9 | 25.8 | 3.0 | 72 |
| 30 | 2.3 | 7.9 | 25.8 | 3.0 | 76 |

The results show a correlation between the drug release and the particle size distribution of the bromocriptine mesylate that was used to prepare the tablet batch. Tablets prepared using bromocriptine mesylate particles where the Dv90 was less than about 20 μm consistently provided a release profile wherein 90% or greater of the drug had been released at about 30 minutes. In contrast, material with a particle size distribution greater than about 20 μm provided variable or low drug release. The correlation between percent drug release and Dv90 is plotted in FIG. 1.

In addition, the particle-size distribution span was also correlated with drug release. The correlation between percent drug release and the particle-size distribution span is plotted in FIG. 2.

Example 7. Micronization of Bromocriptine Mesylate

Bulk batches of bromocriptine mesylate were micronized using a jet mill under a nitrogen atmosphere at a controlled temperature of 0° C. The volume particle size distribution was measured using a Sympatec HELOS H1013 Laser Diffractometer. Table 10 shows the bromocriptine mesylate particle size distribution measured for each batch of bromocriptine mesylate before and after micronization demonstrating that micronization of bulk materials having quite different particle size distributions before micronization resulted in micronized materials with similar particle size distributions. FIG. 3A shows the volume-based particle size distribution measured for the material of Table 6 Entry 1 before micronization and FIG. 3B shows the volume-based particle size distribution measured for the same material after micronization.

The impurity profile (percentage of major impurities), X-ray powder diffraction pattern, I.R. spectra, and differential scanning calorimetry thermograms of the bromocriptine mesylate batches before and after micronization were also investigated. No significant differences were observed, suggesting that the micronization process does not modify the purity or solid state form of the bromocriptine mesylate.

TABLE 10

Bromocriptine Mesylate Particle Size Distributions Before and After Micronization.

| Table | Before Micronization | | | After Micronization | | |
|---|---|---|---|---|---|---|
| Entry | % <1 μm | % <10 μm | % <15 μm | % <1 μm | % <10 μm | % <15 μm |
| 1 | 1 | 19 | 29 | 8 | 97 | 100 |
| 2 | 1 | 55 | 77 | 6 | 98 | 100 |
| 3 | 1 | 31 | 45 | 9 | 98 | 100 |

Example 8. Effect of Micronizing Bromocriptine Mesylate to Improve Drug Release Properties The data provided in Table 11 illustrate the effect of processing bromocriptine mesylate to improve and provide consistent dissolution properties. Bromocriptine mesylate tablets were prepared substantially according to the method described in Example 3 above, wherein said methods include geometric dilution and diffusional blending, and the dissolution of the tablets (n=12) was measured tested in USP Apparatus Type 2 Paddle Method at 50 rpm in 500 mL of 0.1 N hydrochloric acid at 37° C. The tablets prepared were identical except that one batch of tablets (Table Entry 1) was prepared using (non-micronized) bromocriptine mesylate as obtained from the active pharmaceutical ingredient manufacturer (Euticals S.p.a., Milan), whereas another batch of tablets was prepared using the same batch of bromocriptine mesylate but which was further processed by micronization prior to being used for tablet manufacture (Table Entry 2). The data that tablets prepared with micronized bromocriptine mesylate had significantly improved drug release (at 30 minutes) compared to tablets prepared from the same batch of bromocriptine mesylate without micronization.

TABLE 11

Dissolution Results Showing Percentage of Bromocriptine Mesylate Released at 30 Minutes from Different Batches of Bromocriptine Mesylate Tablets.

| Table Entry | Bromocriptine Used | Particle Size Distribution | | | Percent bromocriptine released at 30 minutes (n = 12 Tablets) |
|---|---|---|---|---|---|
| | | Dv10 (μm) | Dv50 (μm) | Dv90 (μm) | |
| 1 | Bromocriptine mesylate without micronization | 1.4 | 5.8 | 26.7 | 69 |
| 2 | Micronized bromocriptine mesylate | 0.7 | 1.5 | 3.1 | 98 |

Example 9. Procedure for the Preparation of a Bromocriptine Mesylate Tablet Formulation Using Micronized Bromocriptine Mesylate Bromocriptine mesylate tablets were prepared having the ingredients listed in Table 12 below.

TABLE 12

Bromocriptine Mesylate Tablet Formulation.

| Ingredient | Quantity (mg/tablet) | Quantity (kg/batch) |
|---|---|---|
| Micronized bromocriptine mesylate USP | 0.945 | 0.84 |
| Corn starch NF | 9.00 | 8.00 |
| Granular anhydrous citric acid USP | 1.35 | 1.20 |
| Anhydrous lactose NF | 77.58 | 69.00 |
| Colloidal silicon dioxide NF | 0.45 | 0.40 |
| Magnesium Stearate NF | 0.675 | 0.60 |
| Total Weight | 90.0 | 80.0 |

Bulk batches of bromocriptine mesylate were micronized using a jet mill under a nitrogen atmosphere at a controlled temperature of 0° C. The volume particle size distribution was measured using a Sympatec HELOS H1013 Laser Diffractometer. The tablets were prepared by geometrical mixing via trituration of micronized bromocriptine mesylate (Euticals S.p.a., Milan) with corn starch as four triturations in a PK BlendMaster™ V-Blender. Sequentially, two sub-loads of granular anhydrous citric acid and corn starch were mixed in a PK BlendMaster™. These two sub-loads were each divided into two equal sub-loads, yielding a total of four sub-loads. Each of the four bromocriptine mesylate triturations was then mixed with adjusted amounts of anhydrous lactose, corn starch and one citric acid/starch corn sub-load in a Fielder PMA 65 mixer to form four premixes [A-D]. A 2.0 kg quantity was removed after Premix A for mixing in a PK BlendMaster™ with colloidal silicon dioxide and magnesium stearate to form a lubricant premix. The four premixes were then loaded in sequential order, with the lubricant premix loaded in between premixes B and C, into an 8 ft$^3$ in-bin hopper; where lubrication/final blending is performed. The lubricated blend was then transferred from the in-bin hopper to a tablet press using a valved transfer chute, and then compressed using a 38-station Hata tablet press.

Example 10. Validation Studies for Tablets Prepared According to Example 9

To validate the manufacturing method, three batches were prepared using substantially the method described in Example 9. Batches of micronized bromocriptine mesylate were obtained from Euticals S.p.a., Milan.

Representative data obtained for tablets prepared from one of the batches is summarized below.

Figure 5:
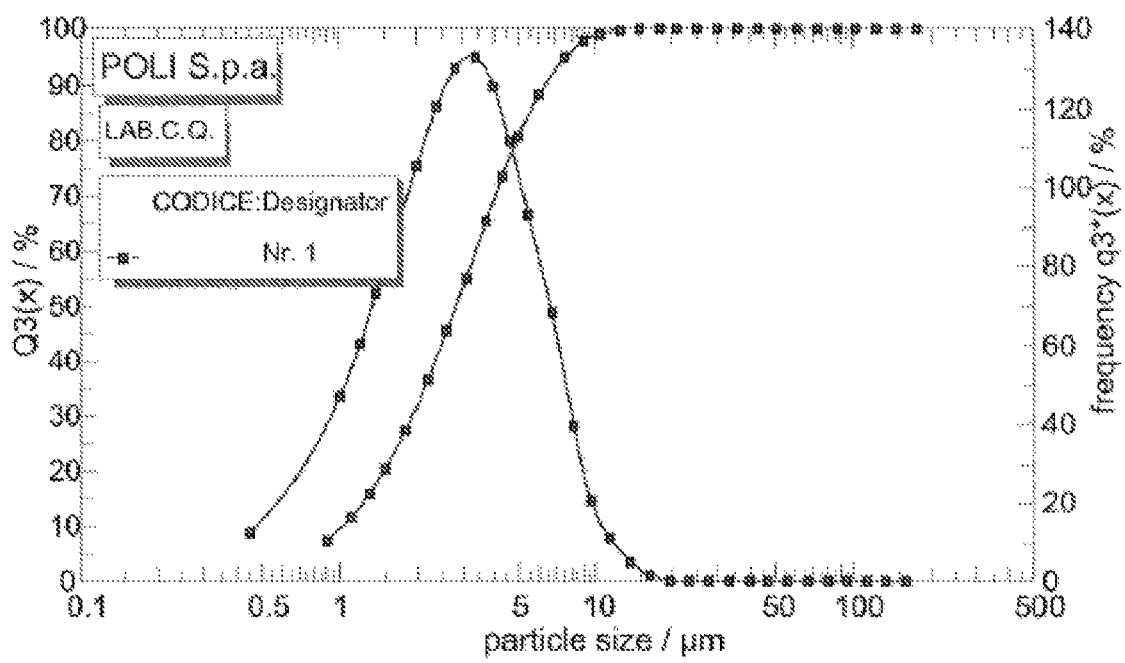
FIG. 5 shows the volume-based particle size distribution measured for a batch of micronized bromocriptine mesylate particles used to manufacture bromocriptine mesylate tablets.

First, Table 13 summarizes the particle size distribution for the micronized bromocriptine mesylate. The particle size distribution for this batch is shown in FIG. 5.

TABLE 13

Bromocriptine Mesylate Particle Size Distributions for Micronized Bromocriptine Mesylate used to Manufacture Tablets as Described in Example 9.
Volume-based Particle Size Distribution

| % <1 μm | % <10 μm | % <15 μm |
|---|---|---|
| 9 | 98 | 100 |

Drug release profiles for samples of the tablets were measured using the USP Apparatus Type 2 Paddle Method at 50 rpm in 500 mL of 0.1 N hydrochloric acid at 37° C. Table 14 below shows the drug release profiles obtained for tablets from a representative batch.

TABLE 14

Drug Release from a Representative Batch of Bromocriptine Mesylate Tablets Prepared as Described in Example 9.

| Time (minutes) | Average % Release (n = 12) |
|---|---|
| 4 | 18 |
| 7 | 34 |
| 10 | 56 |
| 13 | 76 |
| 16 | 88 |
| 19 | 94 |
| 30 | 98 |

In addition, blend uniformity and tablet content uniformity were assessed.

Blend uniformity was assessed by assaying the content of the powdered formulation at twelve locations in the blender following final blending but before tableting. The batch met criteria for blend uniformity.

Tablet content uniformity was evaluated by taking samples at 20 locations throughout the compression process. Three tablets from each time point were then assessed for bromocriptine content. The content uniformity results obtained are summarized in Table 15.

TABLE 15

Content Uniformity Evaluation for a Representative Batch of Bromocriptine Mesylate Tablets Prepared as Described in Example 9 (n = 60 tablets for each batch).

| Bromocriptine Content (% of label) | | | |
|---|---|---|---|
| Mean | Range | RSD % | Pass/Fail |
| 101.4 | 96.6-103.6 | 1.2 | Pass |

Each reference cited in the text of the present application is hereby incorporated by reference in its entirety. A number of embodiments of the invention have been described. Nevertheless, it will be understood that various modifications may be made without departing from the spirit and scope of the invention. Accordingly, other embodiments are within the scope of the following claims.

What is claimed is:

1. A dosage form comprising: bromocriptine and one or more excipients; wherein the dosage form provides for absorption of a substantial amount of bromocriptine through the gastric and/or intestinal mucosa when administered to a subject; wherein the bromocriptine has a Dv10 of less than 2 μm and a volume-based particle size distribution with a span of about 2 or lower; and wherein the dosage form provides a dissolution profile, when tested in USP Apparatus Type 2 Paddle Method at 50 rpm in 500 mL of 0.1 N hydrochloric acid at about 37° C., wherein at least about 80% of the bromocriptine has been released at about 30 minutes.

2. A method of treatment for improving glycemic control in a type 2 diabetes patient comprising orally administering to the patient a dosage form according to claim 1.

3. The method of claim 2, wherein the dosage form is administered in the morning within about two hours after waking.

4. A dosage form comprising: bromocriptine and one or more excipients; wherein the dosage form provides for absorption of a substantial amount of bromocriptine through the gastric and/or intestinal mucosa when administered to a subject; wherein the bromocriptine has a Dv10 of less than 2 μm and a volume-based particle size distribution with a span of about 2 or lower; and wherein the dosage form exhibits a pharmacokinetic profile wherein the time to maximum plasma concentration ($T_{max}$) of bromocriptine is between about 30 and about 60 minutes following oral administration of the dosage form to the subject under fasting conditions or the $T_{max}$ of bromocriptine is between about 90 and about 120 minutes following oral administration of the dosage form to the subject under high fat fed conditions.

5. A method of treatment for improving glycemic control in a type 2 diabetes patient comprising orally administering to the patient a dosage form according to claim 4.

6. The method of claim 5, wherein the dosage form is administered in the morning within about two hours after waking.

7. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a Dv90 of less than 20 μm, a Dv50 of less than 10 μm and a Dv10 of less than 5 μm, and wherein the dosage form provides a dissolution profile, when tested in USP Apparatus Type 2 Paddle Method at 50 rpm in 500 mL of 0.1 N hydrochloric acid at about 37° C., wherein at least about 80% of the bromocriptine has been released at about 30 minutes.

8. A method of treatment for improving glycemic control in a type 2 diabetes patient comprising orally administering to the patient a dosage form according to claim 7.

9. The method of claim 8, wherein the dosage form is administered in the morning within about two hours after waking.

10. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a Dv90 of less than 20 μm, and a Dv50 of less than 10 μm, and wherein the dosage form provides a dissolution profile, when tested in USP Apparatus Type 2 Paddle Method at 50 rpm in 500 mL of 0.1 N hydrochloric acid at about 37° C., wherein at least about 80% of the bromocriptine has been released at about 30 minutes.

11. A method of treatment for improving glycemic control in a type 2 diabetes patient comprising orally administering to the patient a dosage form according to claim 10.

12. The method of claim 11, wherein the dosage form is administered in the morning within about two hours after waking.

13. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a Dv90 of less than 20 μm and a Dv10 of less than 5 μm, and wherein the dosage form provides a dissolution profile, when tested in USP Apparatus Type 2 Paddle Method at 50 rpm in 500 mL of 0.1 N hydrochloric acid at about 37° C., wherein at least about 80% of the bromocriptine has been released at about 30 minutes.

14. A method of treatment for improving glycemic control in a type 2 diabetes patient comprising orally administering to the patient a dosage form according to claim 13.

15. The method of claim 14, wherein the dosage form is administered in the morning within about two hours after waking.

16. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a Dv90 of less than 10 μm, and a Dv10 of less than 5 μm, and wherein the dosage form provides a dissolution profile, when tested in USP Apparatus Type 2 Paddle Method at 50 rpm in 500 mL of 0.1 N hydrochloric acid at about 37° C., wherein at least about 80% of the bromocriptine has been released at about 30 minutes.

17. A method of treatment for improving glycemic control in a type 2 diabetes patient comprising orally administering to the patient a dosage form according to claim 16.

18. The method of claim 17, wherein the dosage form is administered in the morning within about two hours after waking.

19. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a Dv90 of less than 20 μm and wherein the dosage form exhibits a pharmacokinetic profile wherein the time to maximum plasma concentration ($T_{max}$) of bromocriptine is between about 30 and about 60 minutes following oral administration of the dosage form to the subject under fasting conditions or the $T_{max}$ of bromocriptine is between about 90 and about 120 minutes following oral administration of the dosage form to the subject under high fat fed conditions.

20. A method of treatment for improving glycemic control in a type 2 diabetes patient comprising orally administering to the patient a dosage form according to claim 19.

21. The method of claim 20, wherein the dosage form is administered in the morning within about two hours after waking.

22. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a Dv50 of less than 10 μm and wherein the dosage form exhibits a pharmacokinetic profile wherein the time to maximum plasma concentration ($T_{max}$) of bromocriptine is between about 30 and about 60 minutes following oral administration of the dosage form to the subject under fasting conditions or the $T_{max}$ of bromocriptine is between about 90 and about 120 minutes following oral administration of the dosage form to the subject under high fat fed conditions.

23. A method of treatment for improving glycemic control in a type 2 diabetes patient comprising orally administering to the patient a dosage form according to claim 22.

24. The method of claim 23, wherein the dosage form is administered in the morning within about two hours after waking.

25. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a Dv10 of less than 5 μm and wherein the dosage form exhibits a pharmacokinetic profile wherein the time to maximum plasma concentration ($T_{max}$) of bromocriptine is between about 30 and about 60 minutes following oral administration of the dosage form to the subject under fasting conditions or the $T_{max}$ of bromocriptine is between about 90 and about 120 minutes following oral administration of the dosage form to the subject under high fat fed conditions.

26. A method of treatment for improving glycemic control in a type 2 diabetes patient comprising orally administering to the patient a dosage form according to claim 25.

27. The method of claim 26, wherein the dosage form is administered in the morning within about two hours after waking.

28. A dosage form comprising: bromocriptine in micronized form and one or more excipients; wherein the dosage form provides for absorption of a substantial amount of bromocriptine through the gastric and/or intestinal mucosa when administered to a subject; wherein the bromocriptine has a volume-based particle size distribution with a span of less than 3; and wherein the dosage form exhibits a pharmacokinetic profile wherein the time to maximum plasma concentration ($T_{max}$) of bromocriptine is between about 30 and about 60 minutes following oral administration of the dosage form to the subject under fasting conditions or the $T_{max}$ of bromocriptine is between about 90 and about 120 minutes following oral administration of the dosage form to the subject under high fat fed conditions.

29. A method of treatment for improving glycemic control in a type 2 diabetes patient comprising orally administering to the patient a dosage form according to claim 28.

30. The method of claim 29, wherein the dosage form is administered in the morning within about two hours after waking.

* * * * *